US009127254B2

(12) United States Patent
Cohen et al.

(10) Patent No.: US 9,127,254 B2
(45) Date of Patent: Sep. 8, 2015

(54) SCAFFOLDING FOR TISSUE REGENERATION OR REPAIR

(75) Inventors: Smadar Cohen, Beer Sheva (IL); Mona Dvir-Ginzberg, Jerusalem (IL)

(73) Assignee: Ben-Gurion University of the Negev Research and Development Authority, Beer Sheva (IL)

( * ) Notice: Subject to any disclaimer, the term of this patent is extended or adjusted under 35 U.S.C. 154(b) by 1395 days.

(21) Appl. No.: 12/520,008

(22) PCT Filed: Dec. 13, 2007

(86) PCT No.: PCT/IL2007/001545
§ 371 (c)(1),
(2), (4) Date: Dec. 23, 2009

(87) PCT Pub. No.: WO2008/075339
PCT Pub. Date: Jun. 26, 2008

(65) Prior Publication Data
US 2010/0145470 A1    Jun. 10, 2010

Related U.S. Application Data

(60) Provisional application No. 60/875,369, filed on Dec. 18, 2006.

(51) Int. Cl.
*C12N 5/00* (2006.01)
*C12N 5/02* (2006.01)
*C12P 21/04* (2006.01)
*C12M 1/00* (2006.01)
*A01N 1/00* (2006.01)
*A01N 1/02* (2006.01)
*C12N 5/071* (2010.01)
*A61L 27/20* (2006.01)
*A61L 27/38* (2006.01)
*A61L 27/56* (2006.01)

(52) U.S. Cl.
CPC ............... *C12N 5/0671* (2013.01); *A61L 27/20* (2013.01); *A61L 27/3813* (2013.01); *A61L 27/3839* (2013.01); *A61L 27/56* (2013.01); *C12N 2500/25* (2013.01); *C12N 2500/36* (2013.01); *C12N 2500/38* (2013.01); *C12N 2501/11* (2013.01); *C12N 2501/39* (2013.01); *C12N 2533/74* (2013.01)

(58) Field of Classification Search
None
See application file for complete search history.

(56) References Cited

U.S. PATENT DOCUMENTS

| 6,334,968 B1 | 1/2002 | Shapiro et al. |
| 6,479,064 B1 | 11/2002 | Atala |
| 6,793,675 B2 | 9/2004 | Shapiro et al. |
| 6,425,918 B1 | 7/2005 | Shapiro et al. |

FOREIGN PATENT DOCUMENTS

| EP | 1 428 871 | 6/2004 |
| WO | WO 02/46374 | 6/2002 |
| WO | WO 03/072764 | 9/2003 |

OTHER PUBLICATIONS http://medical-dictionary.thefreedictionary.com/p/organoid, definition of organoid, especially from Mosby's Medical Dictionary accessed Jul. 2012.*
Ji-Hyun et al., "Adult human liver derived stem cells differentiate into hepatocytes in a partial hepatectomy-induced liver regeneration", J. Tissue Engineering and Regenerative Medicine 6 (Suppl. 1) : 124 (2012).*
Sandhu et al., "Stem Cell Properties and Repopulation of the Rat Liver by Fetal Liver Epithelial Progenitor Cells", Am. J. Pathology 159 (4) : 1323-1334 (2011).*
Jiang et al., "Efficacy of Engineered Liver Tissue Based on Poly-L-Lactic Acid Scaffolds and Fetal Mouse Liver Cells Cultured With Oncostatin M, Nicotinamide, and Dimethyl Sulfoxide," *Tissue Engineering*, 2004; 10(9-10):1577-1586.
Majka et al., "Numerous Growth Factors, Cytokines, and Chemokines are Secreted by Human CD34(+) Cells, Myeloblasts, Erythroblasts, and Megakaryoblasts and Regulate Normal Hematopoiesis in an Autocrine/Paracrine Manner," *Blood*, 200; 97(10):3075-3085.
Selden et al., "Three-Dimensional in Vitro Cell Culture Leads to a Marked Upregulation of Cell Function in Human Hepatocyte Cell Lines—an Important Tool for the Development of a Bioartificial Liver Machine," *Ann N Y Acad Sci.*, 1999; 875:353-363.
Shimano et al., "Hepatic Oval Cells have the Side Population Phenotype defined 26 by Expression of ATP-Binding Cassette Transporter ABCG2/BCRP1," *Am J Pathol.*, 2003; 163(1):3-9.

(Continued)

*Primary Examiner* — Chris R Tate
*Assistant Examiner* — Douglas F White
(74) *Attorney, Agent, or Firm* — Squire Patton Boggs (US) LLP

(57) ABSTRACT

The present invention relates to bioresorbable scaffolding for tissue regeneration or repair. The present invention describes an epithelial organoid comprising an aggregate of epithelial cells predominantly expressing markers associated with differentiated cell types, and an aggregate which assumes a structure or performs a function associated with an epithelial organ or a fragment thereof. The present invention also provides a method of treating a subject in need of repair or replacement of an organ or a portion thereof; and/or a method of treating a subject with a disease or disorder which impairs or abrogates a liver, kidney, pancreas, thyroid or pituitary function. The present invention also describes an epithelial graft or artificial organ comprising spheroids, organoids or a combination thereof, and a kit for implantable epithelial graft formation comprising organoids.

4 Claims, 6 Drawing Sheets

(56) References Cited

OTHER PUBLICATIONS

Dvir-Ginzberg et al., "Induced differentiation and maturation of newborn liver cells into functional hepatic tissue in macroporous alginate scaffolds" FASEB Journal vol. 22, No. 5, pp. 1440-1449 (2008).
Schubart "Regulation of gene expression in rat hepatocytes and hepatoma cells by insulin: quantitation of messenger ribonucleic acid's coding for tyrosine aminotransferase, tryptophan oxygenase, and phosphoenolpyruvate carboxykinase." Endocrinology vol. 119, No. 4, pp. 1741-1749 (1986).
Schwartz et al., "Multipotent adult progenitor cells from bone marrow differentiate into functional hepatocyte-like cells", The Journal of Clinical Investigation vol. 109, No. 10, pp. 1291-1302 (2002).
Bonner-Weir et al., "In Vitro Cultivation of Human Islets from Expanded Ductal Tissue," *PNAS*, 2000; 97(14):7999-8004.
Brill et al., "Expansion Conditions for Early Hepatic progenitor Cells from Embryonal and Neonatal Rat Livers," *Digestive Diseases and Sciences*, 1999; 44(2):364-371.
Brunk et al. "Assay for Nanogram Quantities of DNA in Cellular Homogenates," *Anal Biochem.*, 1979; 92:497-500.
Cusick et al., "The Effect of Donor and Recipient Age on Engraftment of Tissue-Engineered Liver," Journal of Pediatric Surgery, 1997; 32(2):357-360.
Dabeva et al, "Proliferation and Differentiation of Fetal Liver Epithelial Progenitor Cells After Transplantation into Adult Rat Liver," *Am J Pathol.*, 2000; 156(6):2017-2031.
Dvir-Ginzberg et al., "Liver Tissue Engineering Within Alginate Scaffolds: Effects of cell-Seeding Density on Hepatocyte Viability, Morphology, and Function," *Tissue Engineering*, 2003; 9(4):757-766.
Dvir-Ginzberg et al., "Ultrastructural and Functional Investigations of Adult Hepatocyte Spheroids during In Vitro Cultivation," *Tissue Engineering*, 2004; 10(11/12):1806-1817.
Ehashi et al., "Stimulates Proliferation and Functions of Mouse Fetal Liver Cells in Three-Dimensional Cultures," *J Cell Physiol.*, 2005; 202(3):698-706.
Elkayam et al., "Enhancing the Drug Metabolism Activities of C3A—A Human Hepatocyte Cell Line—By Tissue Engineering Within Alginate Scaffolds," *Tissue Engineering*, 2006; 12(5):1-12.
Faris et al., "Liver Stem Cells: A Potential Source of Hepatocytes for the Treatment of Human Liver Disease," *Artificial Organs*, 2001; 25(7):513-521.
Glicklis et al., "Hepatocyte Behavior Within Three-Dimensional Porous Alginate Scaffolds," *Biotechnology and Bioengineering*, 2000; 67(3):343-353.
Glicklis et al., "Modeling Mass Transfer in Hepatocyte Spheroids via Cell Viability, Spheroid Size, and Hepatocellular Functions," *Biotechnology and Bioengineering*, 2004; 86(6):672-680.
Goodell et al., "Isolation and Functional Properties of Murine Hematopoietic Stem Cells that are Replicating In Vivo," J Exp Med. 1996; 183(4):1797-806.
Hansen et al., "Binding and Cell Spreading on Extracellular Matrix Act at Different Points in the Cell Cycle to Promote Hepatocyte Growth," *Mol. Biol. Cell*, 1994; 5:967-975.
Jiang et al., "Efficacy of Engineered Liver Tissue Based on Poly-L-Lactic Acid Scaffolds and Fetal Mouse Liver Cells Cultured With Oncostatin M, Nicotinamide, and Dimethyl Sulfoxicle," *Tissue Engineering*, 2004; 10(9-10):1577-1586.
Junker et al, "Effect of Adhesion Factors Fibronectin, Laminin, and Type IV Collagen on Spreading and Growth of Transformed and Control Rat Liver Epithelial Cells," *Cancer Res.*, 1987; 47(14):3802-3807.
Kamiya et al., "Maturation OF Fetal Hepatocytes In Vitro by Extracellular Matrices and Oncostatin M: Induction of Trypthophan Oxygenase," Hepatology, 2002; 35(6):1351-1359.
Lazaro et al., "Establishment Characterization, and Long-Term Maintenance of Cultures of Human Fetal Hepatocytes," *Hepatology*, 2003; 38(5):1095-1106.
Majka et al., "Numerous Growth Factors, Cytokines, and Chemokines are Secreted by Human CD34(+) Cells, Myeloblasts, Erythroblasts, and Megakaryoblasts and Regulate Normal Hematopoiesis in an Autocrine/Paracrine Manner," *Blood*, 200; 97(10):3075-3085, 2001.
Michalopoulos et al., "Hepatocytes Undergo Phenotypic Transformation to Biliary Epithelium in organoid Cultures," *Hepatology*, 2002; 36(2):278-283.
Michalopoulos et al., "Liver Regeneration," *Science*, 1997; 276(5309):60-66.
Mooney et al., "Switching From Differentiation to Growth in Hepatocytes: Control by Extracellular Matrix," *Journal of Cell Physiology*, 1992; 151:497-505.
Ojakian et al., "Regulation of Epithelial Cell Surface Polarity Reversal by Beta 1 Integrins," *J Cell Sci.*, 1994; 107( Pt 3):561-576.
Richert et al., "Evaluation of the Effect of Culture Configuration on Morphology, Survival Time, Antioxidant Status and Metabolic Capacities of Cultured rAt Hepatocytes," *Toxicol In Vitro.*, 2002;16(1):89-99.
Risbud et al., "Hydrogel-Coated Textile Scaffolds as Candidate in Liver Tissue Engineering: II. Evaluation of Spheroid Formation and Viability of Hepatocytes," *Biomaterials*, 2003; 14(7):719-731.
Selden et al., "Three-Dimensional In Vitro Cell Culture Leads to a Marked Upregulation of Cell Function in Human Hepatocyte Cell Lines-an Important Tool for the Development of a Bioartificial Liver Machine," *Ann N Y Acad Sci.*, 1999; 875:353-363.
Shapiro et al., "Novel Alginate Sponges for Cell Culture and Transplantation," *Biomaterials*, 1997; 18(8):583-590.
Shimano et al., "Hepatic Oval Cells have the Side Population Phenotype defined 26 by Expression of ATP-Binding Cassette Transporter ABCG2/BCRP1," *Am J Pathol* 2003; 163(1):3-9.
Sugimoto et al., "Hepatic Organoid Formation in Collagen Sponge of Cells Isolated from human Liver Tissues," *Tissue Engineering*, 2005; 11(3/4):626-633.
Tzanakakis et al., "Probing enhanced cytochrome P450 2B1/2 activity in rat hepatocyte spheroids through confocal laser scanning microscopy," Cell Transplant., 2001; 10(3):329-342.
Weadock et al., "Effect of Physical Crosslinking Methods on Collagen-Fiber Durability in Proteolytic Solutions," *J Biomed Mater Res.*, 1996; 32(2):221-226.
Wu FJ et al., "Enhanced Cytochrome P450 IA1 Activity of Self-Assembled Rat Hepatocyte Spheroids," Cell Transplant, 1999; 8(3):233-246.
Zmora et al., "Tailoring the Pore Architecture in 3-D Alginate Scaffolds by Controlling the Freezing Regime During Fabrication," Biomaterials, 2002; 23:4087-4094.

\* cited by examiner a. Newborn Liver Cell Population b. Isolated Adult Hepatocytes

SCAFFOLDING FOR TISSUE REGENERATION OR REPAIR

CROSS-REFERENCE TO RELATED APPLICATIONS

This application is a National Stage of International Application No. PCT/IL2007/001545, filed Dec. 18, 2007, still pending, which claims priority to U.S. Provisional Application No. 60/875,369, filed Dec. 18, 2006. The contents of which are incorporated herein in their entirety.

FIELD OF INVENTION

This invention relates to bioresorbable scaffolding for tissue regeneration or repair. More particularly, the present invention describes: 1) an epithelial organoid comprising an aggregate of epithelial cells predominantly expressing markers associated with differentiated cell types, and an aggregate which assumes a structure or performs a function associated with an epithelial organ or a fragment thereof; 2) a method of treating a subject in need of repair or replacement of an organ or a portion thereof; and/or 3) a method of treating a subject with a disease or disorder which impairs or abrogates a liver, kidney, pancreas, thyroid or pituitary function. The present invention also describes an epithelial graft or artificial organ comprising a scaffold and a progenitor cell population enriched for hepatic, renal, pancreatic, thyroid or pituitary precursor cells, wherein the progenitor cell population forms spheroids, organoids or a combination thereof, and a kit for implantable epithelial graft formation comprising organoids.

BACKGROUND OF THE INVENTION

There is a worldwide shortage of healthy organs for transplant in general, in particular, epithelial-derived organs, such as the liver, pancreas, thyroid and pituitary. For example, a shortage of livers exists for orthotopic organ transplant, as a source of primary hepatocytes for clinical therapies to treat acute and chronic liver failure, and for extracorporeal liver assist devices. Attempts to propagate primary human hepatocytes in culture have met with limited success, because adult human hepatocytes, unlike newborn-derived hepatocytes, do not have a high proliferative capacity. One solution to meet the overwhelming demand for human cells is to employ immortalization strategies to expand the hepatocyte population. Unfortunately, proliferating human hepatocytes tend to lose critical functions such as their ability to metabolize drugs and ammonia in vitro. Another strategy is to use primary porcine hepatocytes or organs for transplants. However, recent concern for the risk of zoonotic infections, such as porcine endogenous retroviruses, may limit the use of xenotreatments in the future.

Bioresorbable scaffolds may be used as a temporary scaffolding for transplanted cells, and thereby allow the cells to secrete extracellular matrix of their own to enable, in the long term, a complete and natural tissue replacement. The macromolecular structure of these scaffolds is selected so that they are completely degradable and are eliminated, once they have achieved their function of providing the initial artificial support for the newly transplanted cells. For these scaffolds to be useful in cell transplantations, they must be highly porous with large surface/volume ratios to accommodate a large number of cells, they must be biocompatible, i.e., non-toxic to the cells that they carry and to the host tissue into which they are transplanted, they must be capable of promoting cellular interactions, promoting the cells to secrete their own extracellular matrix (ECM) components and allowing the retention of the differentiated function of attached cells.

Polysaccharide matrices, such as for example, alginate scaffolds, have been found to be superior to other scaffolds known in the art such as collagen scaffolds in promoting polarized cell-cell and cell-matrix interactions in cultured hepatocytes. They provide adequate sites for the attachment and growth of a sufficient cell mass to survive and function both in vitro and in vivo; support thick layers of cells, such as cell aggregates; and are capable of maintaining the cells in an active functional state before and after implantation/transplantation into a host tissue, at which time the polysaccharide matrix will also be amenable to vascularization from the surrounding tissue. Polysaccharide matrices do not suffer the drawback of limiting the survival and growth of the cells adjacent to the matrix surface as the cells increase in number within the matrix. Another advantage of polysaccharide matrices is that they are biodegradable but degrade only slowly in vivo and thereby permit the cells carried thereby to become established and to form their own tissue matrix at the site of transplant to the point where they no longer require the polysaccharide matrix.

Although an excellent scaffolding, alginate scaffolds seeded with hepatocytes have limited utility in long-term applications. Although hepatocytes initially demonstrate morphological and functional characteristics after 3 days in culture, including spheroid morphology with enhanced cell-cell interactions, the viability of hepatocytes decline rapidly after 8 days in culture.

Therefore, there remains a need for an artificial liver with the same three-dimensional infra-structure as the native organ comprising viable, differentiated cells, and a method of producing such an artificial liver, which may then be used as a transplant, source of hepatocytes for clinical therapy, and/or for extracorporeal liver assist devices.

SUMMARY OF THE INVENTION

In some embodiments, this invention provides an epithelial organoid comprising;
  a. an aggregate of epithelial cells, wherein said cells predominantly express markers associated with differentiated cell types; or
  b. an aggregate of epithelial cells, wherein said aggregate assumes a structure or performs a function associated with an epithelial organ or a fragment thereof; or
  c. a combination thereof;

wherein said organoid is formed in vitro, and more than 95% of said cells are viable in said organoid.

In some embodiments, the organoid can be maintained in culture for up to about 40 days in culture. In some embodiments, the aggregate assumes a structure or performs a function associated with hepatic, renal, pancreatic, thyroid or pituitary tissue. In some embodiments, the aggregate secretes insulin, erythropoietin, a thyroid hormone or a pituitary hormone.

In some embodiments, the organoid comprises cells exhibiting hepatocyte-specific morphology. In some embodiments, the organoid comprises cells exhibiting one or more hepatocellular functions, which in some embodiments comprise albumin secretion, 7-hydroxycoumarin formation, or a combination thereof. In some embodiments, the organoid comprises cells secreting tyrosine amino transferase (TAT), a phosphoenolpyruvate kinase (PEPCK), a tryptophan oxygenase (TO), or a combination thereof.

In some embodiments, the organoid is formed by applying a progenitor cell population enriched for hepatic, renal, pancreatic, thyroid or pituitary precursor cells to a macroporous polyanionic polysaccharide-based scaffold and culturing said scaffold in vitro for a period of time sufficient to form said organoid.

In some embodiments, the organoid is formed by:
  a. applying a progenitor cell population enriched for hepatic, renal, pancreatic, thyroid or pituitary precursor cells to a vessel, in which minimal cellular adhesion to said vessel occurs;
  b. spinning said vessel in (a) at about 25 to about 125 rpm from about 1 to about 14 days to form organoids; and
  c. isolating said organoids.

In some embodiments, the progenitor cell population comprises hematopoietic stem or progenitor cells, hepatoblasts, oval cells, or a combination thereof.

In some embodiments, the progenitor cell population comprises:
  a. from about 1 to about 10% SP-positive cells;
  b. from about 1 to about 10% CD34+ cells; and
  c. from about 70% to about 95% blast cells of endodermal origin.

In some embodiments, this invention provides a mixed cell population comprising:
  a. from about 1 to about 10% SP-positive cells;
  b. from about 1 to about 10% CD34+ cells; and
  c. from about 70% to about 95% blast cells of endodermal origin;
wherein said population is capable of forming epithelial.

In some embodiments, the SP-positive cells, CD34+ cells, blast cells of endodermal origin, or a combination thereof are isolated from fetal or neonatal tissue, or in some embodiments, from adult tissue.

In some embodiments, the population is capable of forming hepatic, renal, pancreatic, thyroid or pituitary tissue.

In some embodiments, this invention provides a spheroid or organoid comprising the mixed cell populations of the invention, which in some embodiments, have a diameter of at least about 50 μm. In some embodiments, this invention provides a spheroid or organoid comprising the mixed cell populations of the invention, which in some embodiments, may further comprise a growth factor.

In some embodiments, this invention provides a process for the preparation of an epithelial graft, said process comprising:
  a. isolating a mixed cell population comprising:
    i. from about 1 to about 10% SP-positive cells;
    ii. from about 1 to about 10% CD34+ cells; and
    iii. from about 70% to about 95% blast cells of endodermal origin;
  b. applying said population in (a) to a vessel, in which minimal cellular adhesion to said vessel occurs,
  c. spinning said vessel in (b) at a range of about 25 to about 125 rpm from about 1 to about 14 days to form spheroids, organoids, or a combination thereof; and
  d. isolating said spheroids, organoids or combination thereof;
whereby said spheroids, organoids or combination thereof form epithelial tissue, when implanted in a subject.

In some embodiments, this invention provides a spheroid, organoid, or combination thereof, or an epithelial graft comprising the spheroid, organoid, or combination thereof, as obtained by the processes of this invention.

In some embodiments, this invention provides a method of treating a subject in need of repair or replacement of an organ or a portion thereof, having liver, kidney, pancreas, thyroid or pituitary function, said method comprising:
  a. isolating a mixed cell population comprising:
    i. from about 1 to about 10% SP-positive cells;
    ii. from about 1 to about 10% CD34+ cells; and
    iii. from about 70% to about 95% blast cells of endodermal origin;
  b. applying said population in (a) to a vessel, in which minimal cellular adhesion to said vessel occurs,
  c. spinning said vessel in (b) at a range of about 25-125 rpm from about 1 to about 14 days to form spheroids, organoids, or a combination thereof; and
  d. isolating said spheroids, organoids or combination thereof, whereby said spheroids, organoids or combination thereof form epithelial tissue, when implanted in a subject; and
  e. implanting said spheroids, organoids or combination thereof in (d) in said subject.

In some embodiments, the subject has a liver disease or disorder, which in some embodiments, is hepatitis, cirrhosis, steatosis, hepatocellular carcinoma, cholestosis, or a combination thereof.

In some embodiments, the subject has a kidney disease or disorder, which in some embodiments is caused or exacerbated by diabetes, high blood pressure, kidney stones, tumors, an enlarged prostate gland, repeated urinary infections, glomerulonephritis, polycystic kidney disease, a genetic malformation, or a combination thereof.

In some embodiments, the subject has a disease or disorder of the pancreas, which in some embodiments is diabetes, pancreatic cancer or pancreatitis.

In some embodiments, the subject has a disease or disorder of the thyroid, which in some embodiments, is a neoplasia or an autoimmune disease.

In some embodiments, this invention provides a method of treating a subject with a disease or disorder, which impairs or abrogates a liver, kidney, pancreas, thyroid or pituitary function, said method comprising:
  a. isolating a mixed cell population comprising:
    i. from about 1 to about 10% SP-positive cells;
    ii. from about 1 to about 10% CD34+ cells; and
    iii. from about 70% to about 95% blast cells of endodermal origin;
  b. applying said population in (a) to a vessel, in which minimal cellular adhesion to said vessel occurs,
  c. spinning said vessel in (b) at 25-125 rpm from about 1 to about 14 days to form spheroids, organoids, or a combination thereof; and
  d. isolating said spheroids, organoids or combination thereof, whereby said spheroids, organoids or combination thereof form epithelial tissue, when implanted in a subject; and
  e. implanting said spheroids, organoids or combination thereof in (d) in said subject.

In some embodiments, the therapeutic protein is insulin, erythropoietin, a thyroid hormone or a pituitary hormone.

In some embodiments, this invention provides an epithelial graft comprising:
  a. a macroporous polyanionic polysaccharide-based scaffold; and
  b. a progenitor cell population enriched for hepatic, renal, pancreatic, thyroid or pituitary precursor cells;
whereby upon culturing said epithelial graft, said progenitor cell population forms spheroids, organoids or a combination thereof in said scaffold.

In some embodiments, the epithelial graft is a hepatic graft.

In some embodiments, the progenitor cell population comprises hematopoietic stem or progenitor cells, hepatoblasts, oval cells, or a combination thereof. In some embodiments, the progenitor cell population is isolated from newborn liver, or in some embodiments, from adult liver.

In some embodiments, the progenitor cell population comprises cells expressing CD34, alpha fetoprotein (AFP), proliferating cell nuclear antigen (PCNA), or a combination thereof.

In some embodiments, the spheroids or organoids comprise cells expressing CK18, e-cadherin, albumin, or a combination thereof. In some embodiments, the spheroids or organoids comprise cells expressing at least one liver enzyme, which in some embodiments is a tyrosine amino transferase (TAT), a phosphoenolpyruvate kinase (PEPCK), a tryptophan oxygenase (TO), or a combination thereof.

In some embodiments, the spheroids or organoids comprise cells exhibiting hepatocyte-specific morphology, or in some embodiments, the spheroids or organoids comprise cells exhibiting one or more hepatocellular functions.

In some embodiments, the alginate scaffold is seeded with from about $1 \times 10^8$ to $1 \times 10^9$ progenitor cells per $cm^3$. In some embodiments, the culturing is conducted in a suitable medium for a period of time of from about 3 days to about 12 months. In some embodiments the culture may further comprise epidermal growth factor (EGF), dexamethasone, insulin, transferrin, selenious acid, linoleic acid, pyruvate, vitamin C, nicotin amid, bovine sera albumin (BSA), HEPES, or a combination thereof.

In some embodiments, the polanionic polysaccharide comprises an alginate, a gellan, a gellan gum, a xanthan, agar, or a carrageenan.

In some embodiment, this invention provides an artificial organ having liver, kidney, pancreas or thyroid function, comprising an epithelial graft of this invention, cultured in a suitable medium for a period of time of from about 6 weeks to about 12 months, or more.

In some embodiments, this invention provides a kit for implantable epithelial graft formation comprising organoids, having liver, kidney, pancreas, thyroid or pituitary function, said kit comprising:
 a. a macroporous polyanionic polysaccharide-based scaffold; and
 b. a progenitor cell population enriched for hepatic, renal, pancreatic, thyroid or pituitary precursor cells.

In some embodiments, the progenitor cell population comprises hematopoietic stem or progenitor cells, hepatoblasts, oval cells, or a combination thereof, or in some embodiments, the progenitor cell population comprises cells expressing CD34, alpha fetoprotein (AFP), proliferating cell nuclear antigen (PCNA), or a combination thereof.

In some embodiments, the kit further comprises a culture medium supplemented with growth factors which promote organoid formation. In some embodiments, such growth factors may comprise In some embodiments, the culturing is conducted in a suitable medium for a period of time of from about 3 days to about 18 months. In some embodiments the culture may further comprise epidermal growth factor (EGF), dexamethasone, insulin, transferrin, selenious acid, linoleic acid, pyruvate, vitamin C, nicotin amid, bovine sera albumin (BSA), HEPES, or a combination thereof.

In some embodiments, this invention provides a process for the preparation of an epithelial graft, said process comprising:
 a. freeze drying a solution comprising a polyanionic polysaccharide to form a macroporous scaffold; and
 b. seeding the scaffold in (a) with a progenitor cell population enriched for hepatic, renal, pancreatic or thyroid precursor cells to yield about $1 \times 10^8$ to $1 \times 10^9$ progenitor cells per $cm^3$ of said scaffold.

In some embodiments, the process further comprises culturing the scaffold in (b) in a suitable medium, supplemented with serum, for a period of time of about 1-5 days. In some embodiments, the process further comprises ascertaining spheroid formation in said scaffold during said period of time. In some embodiments, the process further comprises culturing the scaffold in a serum free medium for a period of time of about 3 days to about 12 months. In some embodiments, the process further comprises ascertaining organoid formation during said period of time.

In some embodiments, this invention provides a method of treating a subject in need of repair or replacement of an organ or a portion thereof, having liver, kidney, pancreas, thyroid or pituitary function, said method comprising:
 a. seeding a macroporous polyanionic polysaccharide-based scaffold with a progenitor cell population enriched for hepatic, renal, pancreatic, thyroid or pituitary precursor cells;
 b. culturing said scaffold in (a) in a suitable medium and for a period of time sufficient to from an artificial organ or a portion thereof, comprising spheroids, organoids, or a combination thereof; and
 c. implanting said artificial organ in (b) in said subject.

In some embodiments, the subject has a liver disease or disorder, which in some embodiments is hepatitis, cirrhosis, steatosis, hepatocellular carcinoma, cholestosis, or a combination thereof.

In some embodiments, the subject has a kidney disease or disorder, which in some embodiments is caused or exacerbated by diabetes, high blood pressure, kidney stones, tumors, an enlarged prostate gland, repeated urinary infections, glomerulonephritis, polycystic kidney disease, a genetic malformation, or a combination thereof.

In some embodiments, the subject has a disease or disorder of the pancreas, which in some embodiments is diabetes, pancreatic cancer or pancreatitis.

In some embodiments, the subject has a disease or disorder of the thyroid, which in some embodiments is a neoplasia or an autoimmune disease.

In some embodiments, this invention provides a method of treating a subject with a disease or disorder, which impairs or abrogates a liver, kidney, pancreas, thyroid or pituitary function, said method comprising:
 a. seeding a macroporous polyanionic polysaccharide-based scaffold with a progenitor cell population enriched for hepatic, renal, pancreatic, thyroid or pituitary precursor cells;
 b. culturing said scaffold in (a) in a suitable medium and for a period of time sufficient to from an artificial organ or a portion thereof, comprising spheroids, organoids, or a combination thereof, which produces an organ specific therapeutic protein;
 c. isolating said therapeutic protein; and
 d. administering said therapeutic protein to the subject.

In some embodiments the therapeutic protein is insulin, erythropoietin, a thyroid hormone or a pituitary hormone.

BRIEF DESCRIPTION OF THE DRAWINGS

FIG. 2 presents morphology, organization and gene expression differences as a result of scaffold composition.

DETAILED DESCRIPTION OF THE PRESENT INVENTION

Figure 1A:
FIG. 1 presents gene expression and side population (SP) cell analysis of isolated cells from newborn liver. (A). Post-isolation gene analysis. Gene expression was compared to GAPDH as a housekeeping gene, which served as a positive control for the assay. (B). FACS Analyses (I & II) represent whole liver cell population.
Figure 1A:

In some embodiments, this invention provides organoids, spheroids or mixed cell populations comprising progenitor cells, which are characterized by the differentiation of progenitor cells to form mature epithelial tissue, in terms of its structure and/or function.

In some embodiments, this invention provides an epithelial organoid comprising:
  a. an aggregate of epithelial cells, wherein said cells predominantly express markers associated with differentiated cell types; or
  b. an aggregate of epithelial cells, wherein said aggregate assumes a structure or performs a function associated with an epithelial organ or a fragment thereof; or
  c. a combination thereof;
wherein said organoid is formed in vitro, and more than 95% of said cells are viable in said organoid.

In some embodiments, the term "organoid" refers, inter glia, to an accumulation of cells, with a phenotype and/or function, consistent with a particular organ. In some embodiments, organoids comprise mixed populations of cells, of a variety of lineages, which are typically found in vivo in a given tissue. In some embodiments, the organoids of this invention are formed in vitro, via any means, whereby progenitor cells differentiate to form aggregates, which in turn may form spheroids, organoids, or a combination thereof. Such aggregates, spheroids or organoids, in some embodiments, assume a structure consistent with a particular organ. In some embodiments, such aggregates, spheroids or organoids, express surface markers, which are typically expressed by cells of the particular organ. In some embodiments, such aggregates, spheroids or organoids, produce compounds or materials, which are typically expressed by cells of the particular organ.

Organoids of this invention are to be distinguished from tissue explants. The former representing an aggregate of cells in vitro, which phenotypically, structurally or functionally resemble a particular organ, which is produced in vitro, while the latter is an excised portion of an organ, which is cultured in vitro. In some embodiments, organoids may be distinguished from explants as a function of their viability in culture, as a function of time in culture. In some embodiments, organoids may be distinguished from explants as a function of their marker expression, product secretion, activity or function, structure, or any other characteristics, as will be appreciated by one skilled in the art.

In some embodiments, spheroids form organoids in culture. In some embodiments, spheroids, as well, are an aggregate of cells in vitro, which phenotypically, structurally or functionally resemble a particular organ, which is produced in vitro, however spheroids have a greater percentage of immature or not-terminally differentiated cells, as compared to organoids of this invention. In some embodiments, spheroids comprise between about 0.1-60% progenitor cells. In some embodiments, spheroids have a range in diameter of from about 50 µm to about 2 mm. In some embodiments, spheroids will produce proteins associated with mature, differentiated tissue, however such proteins are produced at an amount which is less than that produced by organoids. In some embodiments, spheroids will comprise a stem cell population, while organoids will not comprise such populations. In some embodiments, spheroids may share certain characteristics with mature, functional, differentiated tissue, however it will be to a lesser degree than that of the organoids. In some embodiments, organoids represent functional units of tissue. In some embodiments, organoids have a range in diameter of from about 50 µm to about 200 cm. In some embodiments, spheroids, organoids or combinations thereof comprise aggregates of cells having established cell-to-cell contacts, expressing cellular adhesion molecules, and forming intercellular junctions.

In some embodiments, the spheroid forms in culture and can be maintained in culture from about 2 to up to about 12 months in culture. In some embodiments, the organoid can be maintained in culture from about 2 to up to about 12 months in culture.

In some embodiments, the organoids or spheroids are epithelial. In some embodiments, the organoids or spheroids of this invention have a phenotype, structure or function of any epithelial tissue. In some embodiments, such tissue is a gland, and the organoids or spheroids of this invention assume a structure consistent with glandular tissue. According to this aspect, and in some embodiments, the organoids or spheroids of this invention secrete a product consistent with that produced by a particular glandular tissue.

In some embodiments, such tissue is a skin, and the organoids or spheroids of this invention assume a structure consistent with skin, or any components thereof. According to this aspect, and in some embodiments, the organoids or spheroids of this invention secrete a product, or serve a function consistent with that of skin, for example, for covering a wound or lesion. In some embodiments, such tissue is a liver, and the organoids or spheroids of this invention assume a structure consistent with hepatic tissue, an embodiment of which is exemplified herein below, in Example 3, herein below. According to this aspect, and in some embodiments, the organoids or spheroids of this invention secrete a product, or perform a function consistent with that of liver tissue.

In some embodiments, the organoid comprises cells exhibiting hepatocyte-specific morphology. In some embodiments, the organoid comprises cells exhibiting one or more hepatocellular functions, which in some embodiments comprise albumin secretion, 7-hydroxycoumarin formation, or a combination thereof. In some embodiments, the organoid comprises cells secreting tyrosine amino transferase (TAT), a phosphoenolpyruvate kinase (PEPCK), a tryptophan oxygenase (TO), or a combination thereof.

In some embodiments, the organoid is formed by applying a progenitor cell population enriched for hepatic, renal, pancreatic, thyroid or pituitary precursor cells to a macroporous polyanionic polysaccharide-based scaffold and culturing said scaffold in vitro for a period of time sufficient to form said organoid.

In some embodiments, the organoid is formed by:
a. applying a progenitor cell population enriched for hepatic, renal, pancreatic, thyroid or pituitary precursor cells to a vessel, in which minimal cellular adhesion to said vessel occurs;
b. spinning said vessel in (a) at about 65 to about 125 rpm from about 1 to about 14 days to form organoids; and
c. isolating said organoids.

In some embodiments, the aggregate assumes a structure or performs a function associated with hepatic, renal, pancreatic, thyroid or pituitary tissue. In some embodiments, the aggregate secretes insulin, erythropoietin, a thyroid hormone or a pituitary hormone.

In some embodiments, this invention provides mixed cell populations, which form cellular aggregates, which may form a spheroid or organoid as herein described. In some embodiments, the mixed cell population will comprise pluripotent stem cells, which in one embodiment are pluripotent endodermal stem cells.

In some embodiments, the phrase "pluripotent endodermal stem cell(s)" refers to cells capable of self renewal or differentiation into any particular lineage within the endodermal germ layer. In some embodiments, pluripotent endodermal stem cells have the ability to commit within the endodermal lineage from a single cell any time during their life-span. In some embodiments, pluripotent endodermal stem cells may form from any cell type within the endodermal lineage, including, but not limited to, the epithelial lining, epithelial derivatives, and/or parenchyma of the trachea, bronchi, lungs, gastrointestinal tract, liver, pancreas, urinary bladder, kidney, pituitary gland, pharynx, thyroid, thymus, parathyroid glands, tympanic cavity, pharyngotympanic tube, tonsils, and others as appreciated by one skilled in the art.

In some embodiments, the mixed cell populations, aggregates, spheroids and/or organoids of this invention may find use in cell, tissue or organ therapy and/or regeneration and/or their derived products. In some embodiments, mixed cell populations, aggregate, spheroids and/or organoids of this invention may find use in replacement or repair of epithelial linings of the respiratory passages and gastrointestinal tract, the pharynx, esophagus, stomach, intestine and many associated glands, including salivary glands, liver, pancreas and lungs. In some embodiments, the mixed cell populations, aggregates, spheroids and/or organoids of this invention may find use in liver transplantation and pancreas cell replacement, for example in the treatment of cirrhosis or diabetes, representing some embodiments of this invention.

In some embodiments, the mixed cell populations, aggregates, spheroids and/or organoids of this invention may comprise progenitor stem cells (i.e., precursor stem cells, immediate stem cells, and forming [-blast] cells), which are lineage-committed. In some embodiments, the mixed cell populations or aggregates of this invention will comprise a greater percentage of progenitor stem cells or progenitor cells, as compared to the spheroids of this invention, which in some embodiments will comprise a greater percentage of progenitor stem cells or progenitor cells, as compared to the organoids of this invention.

In some embodiments, the mixed cell populations, aggregates, spheroids and/or organoids of this invention may comprise pluripotent stem cells, which are lineage-uncommitted, i.e., they are not committed to any particular mesodermal tissue lineage. They can remain quiescent or be activated to proliferate and/or commit to a particular tissue lineage. In some embodiments, they have the potential to be induced (by general or lineage-specific inductive agents) to form progenitor stem cells for any tissue lineage within the mesodermal line any time during their life span. In some embodiments, the mixed cell populations or aggregates of this invention will comprise a greater percentage of pluripotent stem cells, as compared to the spheroids of this invention, which in some embodiments will comprise a greater percentage of pluripotent stem cells, as compared to the organoids of this invention.

In some embodiments, the progenitor cell population comprises hematopoietic stem or progenitor cells, hepatoblasts, oval cells, or a combination thereof.

In some embodiments, the progenitor cell population comprises:
a. from about 1 to about 10% SP-positive cells;
b. from about 1 to about 10% CD34+ cells; and
c. from about 70% to about 95% blast cells of endodermal origin.

In some embodiments, SP-positive cells may be identified via any means known in the art, for example, using the Hoechst DNA binding dye-based method which relies on the cell's specific ability to expel the permeant fluorescent dye Hoechst 33342 out of the cell, via the ATP-binding cassette transporter subfamily G member 2 (ABCG2), thus being a Hoechst negative cell population. This population may be visualized by a number of means, including flow cytometry, where it is termed "side population" (SP), because of its particular peripheral location upon fluorescence-activated cell sorting In some embodiments, reference to marker expression may be conducted via any means known in the art, utilizing reagents, which probe for such marker expression, for example, via western blot analysis, fluorescence microscopy, FACS analysis, immunomagneto separation, followed by any number of analytic methods, including Northern Blot, RT-PCR, and other methods referenced herein. Any reagent may be used, as will be appreciated by one skilled in the art, for example, and in one embodiment, the use of monoclonal antibodies or polyclonal antibodies, for ascertaining cell marker expression, and quantitation via FACS analysis is means of establishing ratios of cells within a mixed cell population.

In some embodiments, the mixed cell populations or aggregates of this invention mature to form spheroids, organoids and/or differentiated tissue. In some embodiments, such maturation can occur as a result of 3-D cultivation of the mixed cell populations on macroporous polyanionic polysaccharide-based scaffolding. For example, as demonstrated herein, application of a heterogenic newborn liver cell population, comprising hepatoblasts and a small percentage of SP-positive progenitors, to porous non-adhesive alginate scaffolds resulted in hepatocyte terminal differentiation. The hepatocytes were organized in a typical cell layer having 3 distinct surfaces, i.e., an apical surface between two adjacent cells; a baso-lateral surface facing towards ECM deposits and characterized by microvilli; and a third surface devoid of microvilli and facing an internal fibroblastic cell mass.

The acquirement of hepatocyte polarity was accompanied by up-regulation and prolonged maintenance of hepatocellular functions, such as the expression of albumin and mature hepatic liver enzymes. This phenomenon was unique to cultivation in alginate scaffolds, in this embodiment, and was not apparent in the collagen adhesive scaffolds. The alginate scaffold possesses two main features that are conducive for regenerating the hepatic tissue with its distinct cell polarity; the non-adhesive nature of the matrix and its durable macroporous structure, both leading to cell confinement in a defined 3-D milieu.

In some embodiments, the mixed population of cells, aggregates, spheroids and/or organoids of this invention are capable of forming hepatic, renal, pancreatic, thyroid or pituitary tissue.

In some embodiments, this invention provides a spheroid or organoid comprising the mixed cell populations of the invention, which in some embodiments, have a diameter of at least about 85 μm. In some embodiments, this invention provides a spheroid or organoid comprising the mixed cell populations of the invention, which in some embodiments, may further comprise a growth factor, and in some embodiments, have undergone differentiation of at least a portion of the cells in the population.

In some embodiments, this invention provides a process for the preparation of a spheroid, organoid or epithelial graft, said process comprising:
a. isolating a mixed cell population comprising:
    i. from about 1 to about 10% SP-positive cells;
    ii. from about 0.1 to about 10% CD34+ cells; and
    iii. from about 70% to about 95% blast cells of endodermal origin;
b. applying said population in (a) to a vessel, in which minimal cellular adhesion to said vessel occurs,
c. spinning said vessel in (b) at about 65 to about 125 rpm from about 1 to about 14 days to form spheroids, organoids, or a combination thereof; and
d. isolating said spheroids, organoids or combination thereof; whereby said spheroids, organoids or combination thereof form epithelial tissue, when implanted in a subject.

In some embodiments, the vessel is a 250 mL spinner flask, and cells are seeded at a concentration of $5 \times 10^5$ cells/mL. In some embodiments, prior to cell seeding, the vessels are treated with a material to diminish cellular attachment to vessel walls. In some embodiments, the vessel is siliconized by coating with Sigmacote (Sigma), for example, for 1 hour, rinsed with deionized water and sterilized. In some embodiments, the seeded vessels are stirred or rotated at from about 100-175 rpm, for example, and in some embodiments, at 110 rpm, which in some embodiments, are under environmentally controlled conditions, for example, in 5% $CO_2$ at 37° C.

In some embodiments, the vessel is a tissue culture flask, for example a 25 mL T-flask. In some embodiments, the flask is similarly seeded with $5 \times 10^5$ cells/mL. In some embodiments, the seeded flasks are stirred or rotated or at from about 50-175 rpm, for example, and in some embodiments, at 70 rpm, which in some embodiments, are under environmentally controlled conditions, for example, in 5% $CO_2$ at 37° C.

In some embodiments, the choice of vessel, in terms of its shape and/or composition, will reflect considerations of shear stresses and fluid flow within the vessel, which in turn may affect the spheroid and/or organoid formation rate, size and cell viability within the spheroids and/or organoids.

In some embodiments, this invention provides a spheroid, organoid, or combination thereof, or an epithelial graft comprising the spheroid, organoid, or combination thereof, as obtained by the processes of this invention.

In some embodiments, this invention provides an epithelial graft comprising:
a. a macroporous polyanionic polysaccharide-based scaffold; and b. a progenitor cell population enriched for hepatic, renal, pancreatic, thyroid or pituitary precursor cells;

whereby upon culturing said epithelial graft, said progenitor cell population forms spheroids, organoids or a combination thereof in said scaffold.

In some embodiments, the epithelial graft is a hepatic graft.

In some embodiments, the progenitor cell population comprises hematopoietic stem or progenitor cells, hepatoblasts, oval cells, or a combination thereof. In some embodiments, the progenitor cell population is isolated from newborn liver, or in some embodiments, from adult liver.

In some embodiments, the progenitor cell population comprises cells expressing CD34, alpha fetoprotein (AFP), proliferating cell nuclear antigen (PCNA), or a combination thereof.

In some embodiments, the spheroids or organoids comprise cells expressing CK18, e-cadherin, albumin, or a combination thereof. In some embodiments, the spheroids or organoids comprise cells expressing at least one liver enzyme, which in some embodiments is a tyrosine amino transferase (TAT), a phosphoenolpyruvate kinase (PEPCK), a tryptophan oxygenase (TO), or a combination thereof.

In some embodiments, the mixed cell populations, seeded scaffolds, spheroids or organoids comprise cells exhibiting hepatocyte-specific morphology, or in some embodiments, the spheroids or organoids comprise cells exhibiting one or more hepatocellular functions, which is progressively more apparent, in said mixed cell populations, seeded scaffolds, spheroids and organoids, respectively.

In some embodiments, the spheroids or organoids comprise cells expressing genes expressed in the early hepatoblast, such as α-fetoprotein and albumin, or genes expressed around the time of birth or in the immediate postnatal period, such as mdr-1β, OV-6, CD34 which are progressively less apparent as cells differentiate, in said mixed cell populations, seeded scaffolds, spheroids and organoids, respectively. TAT and serine dehydratase are up-regulated with differentiation In some embodiments, the spheroids or organoids comprise cells expressing genes expressed later during fetal liver development (e.g., TAT, TO, PEPCK, glucose-6-phosphatase and 1-antitrypsin), or which is progressively more apparent, in said mixed cell populations, seeded scaffolds, spheroids and organoids, respectively.

In some embodiments, the alginate scaffold is seeded with from about $1\times10^8$ to $1\times10^9$ progenitor cells per $mm^3$ scaffold.

In some embodiments, the culturing is conducted in a suitable medium for a period of time of from about 3 days to about 12 months.

In some embodiments, the polanionic polysaccharide comprises an alginate, a gellan, a gellan gum, a xanthan, agar, or a carrageenan.

In some embodiment, this invention provides a process for the preparation of a spheroid, organoid or epithelial graft, said process comprising:
  a) freeze drying a solution comprising a macroporous polyanionic polysaccharide to form a scaffold; and
  b) seeding the scaffold in (a) with a progenitor cell population enriched for hepatic, renal, pancreatic or thyroid precursor cells to yield about $1\times10^8$ to $1\times10^9$ progenitor cells per $cm^3$ scaffold.

In some embodiments, the process further comprises culturing the scaffold in (b) in a suitable medium, supplemented with serum, for a period of time of about 4 h to 24 h. In some embodiments, the process further comprises ascertaining spheroid formation in said scaffold during said period of time. In some embodiments, the process further comprises culturing the scaffold in a serum free medium for a period of time of about 3 days to about 12 months. In some embodiments, the process further comprises ascertaining organoid formation during said period of time.

According to this aspect of the invention, and in some embodiments, the scaffolding, spheroids, organoids and/or grafts of the present invention can be used as a vehicle for the in situ delivery of biologically active agents. The biologically active agents incorporated into, or included as an additive within, the composition of the present invention can include, without limitation, medicaments, vitamins, mineral supplements, substances used for the treatment, prevention, diagnosis, cure or mitigation of disease or illness, substances which affect the structure or function of the body, or drugs.

The biologically active agents can be used, for example, to facilitate implantation of the composition into a patient and to promote subsequent integration and healing processes. The active agents include, but are not limited to, antibodies, antibody fragments, antibiotics, antifungal agents, antibacterial agents, anti-viral agents, anti-parasitic agents, immunosuppressant agents, growth factors, neurotrophic factors, angiogenic factors, anaesthetics, mucopolysaccharides, metals, cells, proteins, polynucleotides, polypeptides enzymes, degradation agents, lipids, carbohydrates, chemical compounds such as pharmaceuticals and other wound healing agents. The substances can be therapeutic agents, diagnostic materials, and/or research reagents.

Examples of proteins that may be incorporated into or otherwise associated with the scaffolding, spheroids, organoids and/or grafts of the present invention are collagen (of the various types) and fibronectin. The scaffolding, spheroids, organoids and/or grafts of the present invention can be adapted to allow delayed release of the biologically active agents, or controlled release over time.

The scaffolding, spheroids, organoids and/or grafts of the present invention of the present invention, may facilitate tissue ingrowth following implantation and may be infiltrated with nutrient and/or cellular material at the implant site or in cell cultures. Nutrients may also diffuse across the scaffolding, spheroids, organoids and/or grafts of the present invention, for advantageous incorporation.

In some embodiments, the scaffolding, spheroids, organoids and/or grafts of the present invention may comprise cells arising from the ectoderm, mesoderm, or endoderm germ cell layers. In some embodiments, cells from the mesoderm are utilized, to form epithelial tissue. In some embodiments, various cells may be incorporated in the scaffolding, spheroids, organoids and/or grafts of the present invention, for example pancreatic islet cells, blood cells, marrow cells, epithelial cells, dermal cells, fibroblasts and others as known to one skilled in the art. Seeded cells can be autogenic, allogenic, or xenogenic to the patient in which the scaffolding, spheroids, organoids and/or grafts of the present invention are implanted. Seeded cells can be encapsulated or non-encapsulated. The cells can be stem cells or progenitor cells (such as stem cells or progenitor cells of any of the aforementioned differentiated cell types), or mature, differentiated cells.

In some embodiments, cells comprising the mixed cell populations, aggregates, scaffolding, spheroids, organoids and/or grafts of the present invention may be genetically modified or non-genetically modified. In some embodiments, such modification may comprise expression of particular sequences, which will suit a particular application. For example, mixed cell populations, aggregates, scaffolding, spheroids, organoids and/or grafts for applications in treating, repairing or replacing a kidney in a subject in need, may further comprise engineering of at least a portion of cells to secrete erythropoietin, for treating certain subjects in need thereof.

In some embodiments, the term "cell" is intended to include primary cells, cells of cell culture, and cells of cell lines (e.g., cells of tumors or immortalized cells. As will be understood by one of skill in the art, there are over 200 cell types in the human body. The methods, cell populations, scaffolding, aggregates, spheroids, organoids and/or grafts and/or compositions or kits of the present invention may utilize any of these cell types, singly or in combination. Other cells suitable for use with the compositions and methods of the present invention include those disclosed by Spier R. E. et al., eds., The Encyclopedia of Cell Technology (2000), John Wiley & Sons, Inc., and Alberts B. et al., eds., Molecular Biology of the Cell (1994), 3rd ed., Garland Publishing, Inc., e.g., pages 1188-1189, which are incorporated herein by reference in their entireties.

The scaffolds of the present invention may be any shape suitable for the particular in vitro or in vivo application. In some embodiments, a particular shape can be produced utilizing freeze-drying techniques, as described herein. In one embodiment, the cross-sections may be round, elliptical, or irregularly polygonal, depending on the application. Scaffolds of the present invention may be used in virtually all instances when it is desirable to provide a substrate for the growth of cells onto or into a tissue replaceable matrix, either in vitro or in vivo. The scaffold itself may be molded or cut into a specific shape that is applicable for its end usage.

In some embodiments, cells can be stimulated to differentiate by contact with one or more differentiation agents (e.g., trophic factors, hormonal supplements), such as forskolin, retinoic acid, putrescin-transferrin, cholera toxin, insulin-like growth factor (IGF), transforming growth factor (e.g., TGF-α, TGF-β), tumor necrosis factor (TNF), fibroblast growth factor (FGF), epidermal growth factor (EGF), granulocyte macrophage-colony stimulating factor (GM-CSF), hepatocyte growth factor (HGF), hedgehog, vascular endothelial growth factor (VEGF), thyrotropin releasing hormone (TRH), platelet derived growth factor (PDGF), sodium butyrate, butyric acid, cyclic adenosine monophosphate (cAMP), cAMP derivatives (e.g., dibutyryl cAMP, 8-bromo-cAMP), phosphodiesterase inhibitors, adenylate cyclase activators, prostaglandins, ciliary neurotrophic factor (CNTF), brain-derived neurotrophic factor (BDNF), neurotrophin 3, neurotrophin 4, interleukins (e.g., IL-4), interferons (e.g., interferon-gamma), potassium, amphiregulin, dexamethasone (glucocorticoid hormone), isobutyl 3-methyulxanthine, somatostatin, lithium, and growth hormone.

In some embodiments, the terms "a", "an", and "the" includes both singular, and plural, such as at least one, or two or more, on a scale as appropriately understood by one skilled in the art. For example, a reference to "a spheroid" includes more than one such spheroid, a reference to "an organoid" includes more than one such organoid, a reference to "a biological or biologically active agent" includes more than one such agent, a reference to "a cell" includes more than one such cell, and the like.

In some embodiments, the terms "administer", "apply", "transplant", "implant", "deliver", or grammatical variations thereof, are used interchangeably and intended to include all methods known in the art for delivery of the indicated material to a subject. For example, cells cultured according to the methods of the subject invention can be administered locally (e.g., to one or more target anatomical sites), systemically (e.g., through infusion), internally, etc. Cultured cells can be administered to a patient by any method of delivery, such as intravascularly, intracranially, intracerebrally, intramuscularly, intradermally, intravenously, intraocularly, orally, nasally, topically, or by open surgical procedure, depending upon the anatomical site or sites to which the cells are to be delivered. The cells, spheroids, organoids, grafts, etc. of this invention can be administered to various organs, as applicable.

In some embodiments, the term "differentiated", or grammatical variations thereof, refers to cells having a specialized structure or function typical of the cell type found with the target organ, in vivo. In some embodiments, the term "differentiated" is to be understood as partially, as well as fully differentiated cells, which may have a reasonable, or in some embodiments, a substantial amount of their full complement of specialized structure and/or function.

In some embodiment, this invention provides an artificial organ having liver, kidney, pancreas or thyroid function, comprising an epithelial graft of this invention, cultured in a suitable medium for a period of time of from about 6 to 72 weeks.

In some embodiments, the term "artificial organ" refers to a cellular aggregate, which has been cultured in vitro, which shares certain characteristics with endogenous tissue from the indicated organ. In some embodiments, such characteristics will comprise cell surface marker expression, cellular function, which in some embodiments, is evidenced by secreted product profiles or cellular activity. In some embodiments, such characteristics will be reflected in the structure and assembly of the aggregate. In some embodiments, the term "artificial organ" refers to an aggregate, which when implanted in a subject, can compensate, at least partially, for the activity of the indicated organ. For example, artificial pancreata of this invention will secrete insulin when implanted in a subject.

In some embodiments, the artificial organs of this invention are any organs comprising epithelial cells. In some embodiments, the artificial organs of this invention will comprise an artificial kidney, liver, thyroid, pancreas, pituitary or skin.

In some embodiments, this invention provides a kit for implantable epithelial graft formation comprising organoids, having liver, kidney, pancreas, thyroid or pituitary function, said kit comprising:
  a. a macroporous polyanionic polysaccharide-based scaffold; and
  b. a progenitor cell population enriched for hepatic, renal, pancreatic, thyroid or pituitary precursor cells.

In some embodiments, the progenitor cell population comprises hematopoietic stem or progenitor cells, hepatoblasts, oval cells, or a combination thereof, or in some embodiments, the progenitor cell population comprises cells expressing CD34, alpha fetoprotein (AFP), proliferating cell nuclear antigen (PCNA), or a combination thereof. These cells possess to some extent the SP phenotype, as previously described and illustrated in FIG. 1.

In some embodiments, the kit further comprises a culture medium supplemented with growth factors which promote organoid formation. In some embodiments, such growth factors may comprise epidermal growth factor (EGF), dexamethasone, insulin, transferring, selenious acid, linoleic acid, pyruvate, vitamin C, pyruvate, bovine sera albumin (BSA), or a combination thereof. In some embodiments, the mixed cell populations, aggregates, scaffolding, spheroids, organoids, grafts, as well as kits of the present invention may comprise any growth factor or additive, as herein described.

In some embodiments, the mixed cell populations, aggregates, scaffolding, spheroids, organoids, grafts and/or kits of the present invention are used for, or methods are directed to treating a particular disease, disorder or condition in a subject.

In one embodiment, the term "treat" or other grammatical forms thereof, refers to suppressing, inhibiting, preventing, or delaying the onset of symptoms, reducing the severity of symptoms, reducing the severity of an acute episode, reducing the number of symptoms, reducing the incidence of disease-related symptoms, reducing the latency of symptoms, ameliorating symptoms, reducing secondary symptoms, reducing secondary infections, prolonging patient survival, preventing relapse to a disease, decreasing the number or frequency of relapse episodes, increasing latency between symptomatic episodes, increasing time to sustained progression, expediting remission, inducing remission, augmenting remission, speeding recovery, or increasing efficacy of or decreasing resistance to alternative therapeutics.

In one embodiment, symptoms are primary, while in another embodiment, symptoms are secondary. In another embodiment, "symptoms" may be any manifestation of a disease or pathological condition, comprising inflammation, swelling, fever, pain, bleeding, itching, runny nose, coughing, headache, migraine, difficulty breathing, weakness, fatigue, drowsiness, weight loss, nausea, vomiting, constipation, diarrhea, numbness, dizziness, blurry vision, muscle twitches, convulsions, etc., or a combination thereof.

In one embodiment, "treating" refers to both therapeutic treatment and prophylactic or preventative measures, wherein the object is to prevent or lessen the targeted pathologic condition or disorder as described hereinabove. Thus, in one embodiment, treating may include suppressing, inhibiting, preventing, treating, or a combination thereof.

In some embodiments, this invention provides a method of treating a subject in need of repair or replacement of an organ or a portion thereof, having liver, kidney, pancreas, thyroid or pituitary function, said method comprising:
  a. isolating a mixed cell population comprising:
    i. from about 1 to about 10% SP-positive cells;
    ii. from about 1 to about 10% CD34+ cells; and
    iii. from about 70% to about 95% blast cells of endodermal origin;
  b. applying said population in (a) to a vessel, in which minimal cellular adhesion to said vessel occurs,
  c. spinning said vessel in (b) at 110 rpm from about 1 to about 14 days to form spheroids, organoids, or a combination thereof; and
  d. isolating said spheroids, organoids or combination thereof, whereby said spheroids, organoids or combination thereof form epithelial tissue, when implanted in a subject; and
  e. implanting said spheroids, organoids or combination thereof in (d) in said subject.

In some embodiments, the subject has a liver disease or disorder, which in some embodiments, is hepatitis, cirrhosis, steatosis, hepatocellular carcinoma, cholestasis, or a combination thereof.

In some embodiments, the liver disease or disorder or condition is Alagille Syndrome, alpha-1-antitrypsin deficiency, amebic liver abscess, autoimmune hepatitis, biliary atresia, cancer of the liver, chronic hepatitis, coccidioidomycosis; disseminated, delta agent (Hepatitis D), drug-induced cholestasis, fatty liver or steatorrhoeic hepatosis or steatosis, galactosemia, Gilbert's Syndrome, hemochromatosis, hepatitis A, hepatitis B, hepatitis C, hepatocellular carcinoma, liver cysts, liver disease due to alcohol, neonatal hepatitis, non-alcoholic steatohepatitis, porphyria, primary biliary cirrhosis, primary biliary cirrhosis, primary sclerosing cholangitis, pyogenic liver abscess, Reye's syndrome, sarcoidosis, sclerosing cholangitis, type I glycogen storage disease, tyrosinemia, Wilson's disease, or combinations thereof. In some embodiments, the subject is in need of a transplant of hepatic tissue.

In some embodiments, the subject has a kidney disease or disorder, which in some embodiments is caused or exacerbated by diabetes, high blood pressure, kidney stones, tumors, an enlarged prostate gland, repeated urinary infections, glomerulonephritis, polycystic kidney disease, a genetic malformation, or a combination thereof.

In some embodiments, the kidney disease, disorder or condition is acidosis, acute renal failure, agenesis, Alport syndrome, amyloidosis, analgesic nephropathy, Bartter syndrome, Berger's disease, chronic pyelonephritis, chronic renal failure, chronic renal insufficiency, Ccescentic nephritis, cysts in the kidneys, mesangiocapillary glomerulonephritis (MCGN), diabetes insipidus, diabetic nephropathy, Fabry disease, Fanconi syndrome, fibrillary nephritis, Gitelman syndrome, glomerulonephritis, Goodpasture disease/syndrome, hypernephroma, hepatorenal syndrome, hypertension, hypoplasia, lupus, medullary sponge kidney, membranous nephropathy, mesangiocapillary glomerulonephritis MCGN, myeloma, obstruction and obstructive nephropathy, polyarteritis, PKD—polycystic kidney disease, polydipsia, polyuria, post-infectious glomerulonephritis, pyelonephritis, Wegener's granulomatosis, Wilm's tumour, or a combination thereof.

In some embodiments, the subject has a disease or disorder of the pancreas, which in some embodiments is diabetes, pancreatic cancer or pancreatitis. In some embodiments, the disease or disorder is Type II diabetes, Type I diabetes, diabetes insipidus, diabetes mellitus, maturity-onset diabetes, juvenile diabetes, insulin-dependant diabetes, insulin resistance, non-insulin dependant diabetes, malnutrition-related diabetes, ketosis-prone diabetes, ketosis-resistant diabetes, amyloidosis or combinations thereof.

In some embodiments, the subject has a disease or disorder of the thyroid, which in some embodiments, is a neoplasia or an autoimmune disease. In some embodiments, the disease disorder or condition of the thyroid may comprise, inter alia, thyroiditis, including Hashimoto's thyroiditis, euthyroid sick syndrome, •hyperthyroidism, •hypothyroidism, •silent lymphocytic thyroiditis, simple nontoxic goiter, •subacute thyroiditis, •thyroid cancers, or others as known in the art.

In some embodiments, the subject has a disease or disorder of the pituitary gland, which in some embodiments includes, inter alia, central diabetes insipidus, •galactorrhea, generalized hypopituitarism, •gigantism and acromegaly, •popituitarism in children resulting in short stature, •pituitary lesions, or •selective pituitary hormone deficiencies, such as deficiencies in growth hormone, gonadotropin, Kallmann syndrome, isolated ACTH deficiency, isolated ACTH deficiency, isolated prolactin deficiency, isolated thyroid-stimulating hormone (TSH) deficiency, which in turn may also reflect a disease or disorder of the thyroid.

In some embodiments, this invention provides a method of treating a subject with a disease or disorder, which impairs or abrogates a liver, kidney, pancreas, thyroid or pituitary function, said method comprising:
  a. isolating a mixed cell population comprising:
    i. from about 1 to about 10% SP-positive cells;
    ii. from about 1 to about 10% CD34+ cells; and
    iii. from about 70% to about 95% blast cells of endodermal origin;
  b. applying said population in (a) to a vessel, in which minimal cellular adhesion to said vessel occurs, c. spinning said vessel in (b) at 110 rpm from about 1 to about 14 days to form spheroids, organoids, or a combination thereof; and d. isolating said spheroids, organoids or combination thereof, whereby said spheroids, organoids or combination thereof form epithelial tissue, when implanted in a subject; and e. implanting said spheroids, organoids or combination thereof in (d) in said subject.

In some embodiments, the therapeutic protein is insulin, erythropoietin, a thyroid hormone or a pituitary hormone.

In some embodiments, this invention provides a method of treating a subject in need of repair or replacement of an organ or a portion thereof, having liver, kidney, pancreas, thyroid or pituitary function, said method comprising:

a. seeding a macroporous polyanionic polysaccharide-based scaffold with a progenitor cell population enriched for hepatic, renal, pancreatic, thyroid or pituitary precursor cells;

b. culturing said scaffold in (a) in a suitable medium and for a period of time sufficient to from an artificial organ or a portion thereof, comprising spheroids, organoids, or a combination thereof; and c. implanting said artificial organ in (b) in said subject.

In some embodiments, the subject has a liver disease or disorder, which in some embodiments is hepatitis, cirrhosis, steatosis, hepatocellular carcinoma, cholestosis, or a combination thereof.

In some embodiments, the subject has a kidney disease or disorder, which in some embodiments is caused or exacerbated by diabetes, high blood pressure, kidney stones, tumors, an enlarged prostate gland, repeated urinary infections, glomerulonephritis, polycystic kidney disease, a genetic malformation, or a combination thereof.

In some embodiments, the subject has a disease or disorder of the pancreas, which in some embodiments is diabetes, pancreatic cancer or pancreatitis.

In some embodiments, the subject has a disease or disorder of the thyroid, which in some embodiments is a neoplasia or an autoimmune disease.

In some embodiments, this invention provides a method of treating a subject with a disease or disorder, which impairs or abrogates a liver, kidney, pancreas, thyroid or pituitary function, said method comprising:

a. seeding a macroporous polyanionic polysaccharide-based scaffold with a progenitor cell population enriched for hepatic, renal, pancreatic, thyroid or pituitary precursor cells;

b. culturing said scaffold in (a) in a suitable medium and for a period of time sufficient to from an artificial organ or a portion thereof, comprising spheroids, organoids, or a combination thereof, which produces an organ specific therapeutic protein;

c. isolating said therapeutic protein; and d. administering said therapeutic protein to the subject.

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

EXAMPLES

Materials and Methods

Scaffold Preparation

Macroporous alginate and collagen scaffolds possessing a similar internal micro structure (90% porosity; 50-100 μm pore size, 0.04 cm$^3$ volume) were utilized for cell cultivation. The alginate (MVG, FMC Biopolymer, Norway) scaffolds were prepared from 1% (w/v) sodium alginate cross-linked with 0.2% (w/v) D-gluconic acid, hemi-calcium by a freeze-dry technique (Shapiro L, and Cohen S. Biomaterials. 1997; 18: 583-90). Collagen (calf skin) scaffolds were prepared from 1% (w/v) solution in 0.2% (v/v) acetic acid and freeze-dried as the method for preparing alginate scaffolds (Shapiro and Cohen 1997). The collagen scaffolds were further subjected to UV cross-linking to enhance their stability (Weadock et al. J Biomed Mater Res. 1996; 32(2):221-6).

Isolation and Culture of Newborn Liver Cells

The study was performed with the approval and according to the guidelines of the Institutional Animal Care and Use Committee. Newborn liver cells were isolated from Sprague Dawley rats (Brill et al. Digestive Diseases and Sciences. 1999; 44(2):364-71), with slight modifications. The livers were dissected and then chelated in HBSS buffer containing 0.5 mM EGTA, 20 mM HEPES, pH=7.4 (solution A) for 15 min, at 25° C., using a magnetic stirrer. The step was repeated several times using fresh solution A to enhance tissue dissociation. Then, enzymatic digestion was performed by suspending the disintegrating tissues in solution B (HBSS, 5 mM $CaCl_2$, 80 U/ml Collagenase W, 0.8 mM $MgCl_2$, 20 mM HEPES, pH=7.4), at 37° C., for 10-15 min, using a magnetic stirrer. The resulting Cell suspension was centrifuged (5 min, 45 g, 4° C.) and the supernatant was collected into a fresh tube. The pellet underwent 4-6 additional collagenase digestion steps. The supernatants, collected from each digestion step, were gathered, centrifuged (10 min, 680 g, 4° C.), and resuspended for 5 min with AcK (0.15 M $NH_4Cl$, 1 mM $KHCO_3$, 0.1 mM $Na_2EDTA$, pH=7.2-7.4) to remove red blood cell debris. Following centrifugation (10 min, 680 g, 4° C.), the pellet was resuspended with cold solution C (HBSS containing 5 mM $CaCl_2$ and 10 mg/mL bovine serum albumin (BSA), pH=7.4). The supernatant was twice sedimented (10 min, 680 g, 4° C.), and the pellets were collected and combined with the initial pellet and resuspended in culture medium. Following isolation, the cells were immunostained for hepatic markers; albumin and cytokeratin 18; the latter serves as a marker for fully differentiated hepatocytes (Lazaro et al. Hepatology. 2003; 38(5): 1095-106).

The liver cells were seeded into the macro-porous scaffolds via a 2-round centrifugation method (Dvir-Ginzberg et al. Tissue Engineering. 2003; 9:757-66) to yield a final cell density of $125 \times 10^6$ cells/cm$^3$. The cell constructs were cultured in William's E medium, supplemented with 10 mmol/L nicotine amide, 20 mmol/L HEPES, 0 units/ml penicillin/streptomycin, 2 mmol/L glutamine, 17 mmol/L $NaHCO_3$ (Sigma Chemical Co.), 550 mg/L pyruvate (Sigma Chemical Co.), 0.2 mmol/L ascorbic acid-2-phosphate (Sigma Chemical Co.), 14 mmol/L glucose (Sigma Chemical Co.), $10^{-7}$ mol/L dexamethasone (Sigma Chemical Co.), 20 ng/ml EGF (Epidermal Growth Factor; Sigma Chemical Co.), 5 mL of ITS+ premix (6.25 μg/mL insulin, 6.25 μg/mL transferrin, 6.25 ng/mL selenious acid, 1.25 mg/mL BSA and 5.35 ng/mL linoleic acid). The media and supplements were purchased from Biological Industries, Kibbutz Beit Ha'Emek (Israel), unless otherwise specified.

During the initial 4 hours after cell seeding, the medium was supplemented with 5% (v/v) fetal calf serum (FCS) to enhance cell recovery. Later on, the medium was replaced with serum-free medium, which was replaced every 2 days during cultivation. The constructs were incubated in a 95% humidified atmosphere, 5% $CO_2$, 95% air, at 37° C.

Flow Cytometer Analysis (FACS) for Side Population (SP) Progenitor Cells

SP was analyzed following isolation of the newborn liver cells by flow cytometry (Goodell et al. J Exp Med. 1996; 183(4): 1797-806). Briefly, the cells were sedimented (820 g, 10 min, 4° C.), resuspended with DMEM containing 2 (v/v %) FCS and 10 mM HEPES, followed by addition of Hoechst 33342 (Sigma, Israel), at a final concentration of 5 µg/ml. The cells were incubated at 37° C. for 90 min, then centrifuged (820 g, 10 min, 4° C.) and resuspended with HBSS containing 2 (v/v %) FCS and 10 mM HEPES. To confirm the SP phenotype, 2 duplicate samples (n=4) were blocked with verapamil (50 µM final concentration) and incubated with Hoechst 33342 at 37° C. for 90 min. Hoechst was excited at 350 nm, using 450/20 and 670/20 optical filters (FACS-Vantage BD, Santa Clara, Calif., US). Data was analyzed using the Cell Quest software (BD). The SP positive cells appeared at the lower left area of the screen and gated after tracking their disappearance following incubation with verapamil, which is a Hoechst 33342 efflux pump blocker.

Cell Morphology and Distribution in Scaffolds by Fluorescence Microscopy

The cell constructs were stained with 5 µg/ml fluorescein diacetate (FDA), which stains viable cell cytoplasm green and viewed under an inverted fluorescence microscope (Model 1×70, Olympus, Hamburg, Germany), equipped with 490-nm band-pass filter with a 510-nm cutoff filter for fluorescence emission.

Histology, Immunocytochemistry and Transmitting Electron Microscopy

The 3-D cell constructs from day 3, day 14 (week 2) and day 42 (week 6) were fixed in 70%, 90% and 100 v/v % ethanol (1 hour in each solution), embedded in paraffin and sectioned into horizontal cross sections (5-µm thickness). The sections were stained with Hematoxylin and Eosin (H&E). Cross sections of the collagen constructs were additionally stained with Masson tricromica (with aniline blue), according to the manufacturers instructions (Bio-Optica, Italy). Spheroid mean diameter was calculated after visual inspection under an inverted light microscope (n=18).

To detect hepatocytes, the following antibodies were applied: monoclonal mouse anti rat CK18 (Dako, Denmark) and monoclonal mouse anti rat albumin (DakoCytomation, Denmark). In addition, the sections were stained for monoclonal mouse anti rat CK19 (DakoCytomation, Denmark); monoclonal rabbit anti-rat von-Willebrand Factor (Dako, Denmark), and polyclonal mouse anti-rat vimentin (Zymed, Israel) to detect bile cells, endothelial cells and fibroblasts, respectively. For evaluating epithelial cell-cell contact, the samples were stained with monoclonal rabbit anti-rat E-cadherin (Zymed, Israel). ECM deposition for laminin was tested by monoclonal mouse anti-rat laminin (Chemicon International, Germany). Apoptosis was detected by staining with polyclonal rabbit anti-rat cleaved caspase 3 (Biocare Medical, US). Proliferating cells were detected by applying monoclonal anti-rat proliferating cell nuclear antigen (PCNA) clone PC 10 (DakoCytomation, Denmark). Positive and negative controls were obtained from newborn, adult liver tissue samples and empty scaffold sections, respectively. Detection of antigen-antibody binding was obtained by the DakoCytomation EnVision+ System, based on horseradish peroxidase labeled polymer, using 3,3'-diaminobenzidine tetrahydrochloride as a substrate.

TABLE 1

Antibodies used for immunocytochemistry

| Antibody | Host | Reports | Working Dilution | Source |
|---|---|---|---|---|
| Albumin | mouse | Albumin production | 1:10 | Dako, Glostrup, Denmark |
| Monoclonal CK18 | mouse | Hepatocytes | 1:25 | Dako, Glostrup, Denmark |
| Monoclonal CK19 | mouse | Bile Cells | 1:50 | Dako, Glostrup, Denmark |
| Monoclonal Von Willibrand | rabbit | Endothelial cells | 1:200 | Dako, Glostrup, Denmark |
| Monoclonal E-Cadherin | rabbit | Epithelial cell-cell interactions | 1:100 | Zymed, Carlsbad, CA |
| Monoclonal PCNA | Clone PC10 | Proliferating cells | 1:200 | Dako, Glostrup, Denmark |
| Polyclonal Cleaved Caspase 3 | rabbit | Apoptotic cells | 1:50 | Biocare Medical, Concord, CA |
| Monoclonal Laminin | mouse | ECM deposition | 1:100 | Chemicon Temecula, CA |
| Polyclonal Vimentin | mouse | Fibroblast-like cells | 1:100 | Zymed, Carlsbad, CA |

Ultrastructural Analysis on cell constructs from week 6 in culture (n=10) was carried out after fixation and sectioning into 1-µm sections and staining with uranyl acetate and lead citrate, according to standard procedure by a trained technician. Five grids from 2 samples were observed from each data point, from two different experiments. Micrographs were taken of representative samples using a TEM model TEM 1230 (JEOL, Germany).

Gene Expression

Three cell constructs per sample were collected using centrifugation (4000 g, 5 min, 4° C.) and stored at −70° C. The cells within the constructs were burst by denaturing solution (EZ-RNA, Beit-HaEmek, Israel) and ground using a plastic rod. The rest of RNA isolation procedure was carried out according to EZ-RNA manufacturer's instructions (Beit-HaEmek, Israel). The precipitant was dried and DEPC (Diethylpurocarbonate) treated DDW was added. RNA was later quantified using a Nanodrop reader (Nanodrop Inc. US).

One microgram aliquots of total RNA were reverse transcribed into cDNA using the reverse-iT $1^{st}$ strand synthesis kit (ABgene, UK), according to the manufacturer's instructions. The resulting cDNA was then used in traditional PCR reactions utilizing the Thermo-start DNA polymerase kit (AB gene, UK) following the manufacturer's instructions. Primer sequences (Table 1) were established using the PubMed gene bank and NCBI Blast. Reaction mixture comprised: 1×PCR buffer, 1.5 mM $MgCl_2$, 0.8 mM dNTP mix, 0.5 mM forward and reverse primer mix, I cDNA and 1.25 units of Thermo- Start DNA polymerase. GAPDH was used as an internal control gene. The resulted transcripts (25 μl-sample) were separated on 1.2% agarose gel (wt % in TAE buffer) containing 1 μg/ml ethidium bromide for UV visualization.

TABLE 2

PCR primers used for RT-PCR and reaction* conditions

| Gene | Acc. No. | Forward Primer<br>Reverse Primer | Amplicon size (bp) | Annealing Temp (° C.) |
|---|---|---|---|---|
| Albumin | NM134326 | 5'-TTCCTGAAGCTCAGAGACTG-3'<br>5'-TGGCGAAGCAGTTATCCTTG-3' | 390 | 55 |
| TAT | NM012668 | 5'-ATTTCCCGGAATTCGAGAACGA-3'<br>5'-GACGGGTGAGGGCTTATTTGTC-3' | 234 | 58 |
| PEPCK | K03243 | 5'-CCAGCCAGAGTATATTCACA-3'<br>5'-GCTTTCTCGAAGTCCTCTTC-3' | 261 | 55 |
| AFP | M18351 | 5'-TGCCCGACAGAGAAAAATATG-3'<br>5'-GCAGTTTCTGGAAAGTGGAAG-3' | 312 | 56 |
| GAPDH | NM017008 | 5'-TGGTGCTGAGTATGTCGTG-3'<br>5'-TGGCATGGACTGTGGTCAT-3' | 272 | 55 |
| TO | NM022403 | 5'-TGTAGTTCAGAGACGTGATG-3'<br>5'-GAACTGCTCACCAAGCTTTA-3' | 245 | 50 |
| PCNA | NM022381 | 5'-TCCCAGACAAGCAATGTTGA-3'<br>5'-AGGTACAAACTTGGTGACAG-3' | 332 | 51 |
| CD34 | XM223083 | 5'-ACTTTCCAGCAAACTCCAGC-3'<br>5'-AGCAGGACTCCCGAGGTAAC-3' | 147 | 53 |

*All reactions involved 35 cycles

Biochemical Assays

DNA content was measured as indication of construct cellularity. Fluorescent enhancement following the formation of 4',6-diamido-2-phenylindole (DAPI) complexes with DNA[22] was monitored via a fluorimeter (Varian, CaryEclipse, US). Briefly, cell-seeded scaffolds (n=3-4 per data point) were rinsed in PBS, frozen in liquid nitrogen and stored at –80° C., until analysis. After thawing, samples were mixed with 1 mL of 1M NaOH, and were incubated for 30 min, at 70° C. After incubation the pH was adjusted to 7.0, 850 μL of 100 ng/ml DAPI solution was added to each 150 μl, sample and the mixture was read at 360-nm excitation and 470-nm emission. The cell number in samples was determined by comparison to standard curves, in which DNA content was measured for a range of known cell concentrations.

Albumin secretion from the cell construct during cultivation was determined by an enzyme-linked immunosorbent assay (ELISA), using antibodies specific to rat albumin (Organon-Teknika Corporation/Cappel)[8]. Rat albumin (Organon-Teknika Corporation/Cappel) was used for establishing the standard curve. Specific secretion rates were calculated from albumin levels divided by the cell number derived from DNA quantification assay.

To evaluate phase I basal detoxification ability, which is associated with many P450 isoenzymes (i.e. CYP2B6, CYP2A6, CYP2E1, CYP1A1), newborn hepatocytes within collagen and alginate 3-D scaffolds were monitored throughout cultivation. The cell constructs were incubated for 24 h in media containing 0.01 mM dicumarol (2 mL per scaffold) humidified atmosphere at 37° C., 5% $CO_2$ and 95% air, to induce the reaction. Then, the media was replaced with 400 μL PBS containing 0.01 mM dicumarol as a negative control and PBS containing 0.01 mM Dicumarol and the substrate 1.1 mM 7-ethoxycoumarin as positive control, for 4 h incubation. 100 μl aliquots/well were removed to a new well of an opaque 96-well plate, thereafter 100 μl of acetate buffer solution (0.01 M sodium acetate, 0.01 M glacial acetic acid) containing 400 units of glucoronide (Roche) to reverse conjugation from secreted 7-hyroxycoumarin (1 h, 37° C.). 40 μL of glycine NaOH buffer was added (17 M Glycine, 1.7M NaOH) to each well and immediately read in a fluorimeter (excitation 390 nm, emission 440 nm). The percentage conversion was extrapolated from a standard curve for known 7-hydroxycoumarin concentrations. Specific rates of conversion per data point, were calculated per $10^6$ cells determined in DNA quantification.

Statistical Analysis

Statistical analysis of data was preformed using the one and one-way ANOVA, assuming confidence levels 95% (p<0.05) for statistical significance. Student's t-tests were carried out to determine differences between two treatments within a group. The error bars around the mean value in figures indicate the standard deviation of the data point.

Example 1

Post Isolation Cell Characterization

Gene expression was used to characterize the cell type and the percentage of progenitors in the isolated newborn liver cell population (FIG. 1A), FACS analysis was performed to identify side population (SP) progenitors (FIG. 1B) and immunostaining for hepatic markers albumin and CK18 determined further characterized the cell population of the isolated newborn liver cell population.

The newborn liver cell population expressed AFP, PCNA, CD34, and albumin, indicating the presence of proliferating hepatoblasts as well as hematopoeitic progenitors. They did not express adult liver-specific enzymes, such as TO. In comparison, the isolated adult hepatocytes expressed albumin, TAT, PEPCK and TO, but not AFP and CD34.

Figure 1B:
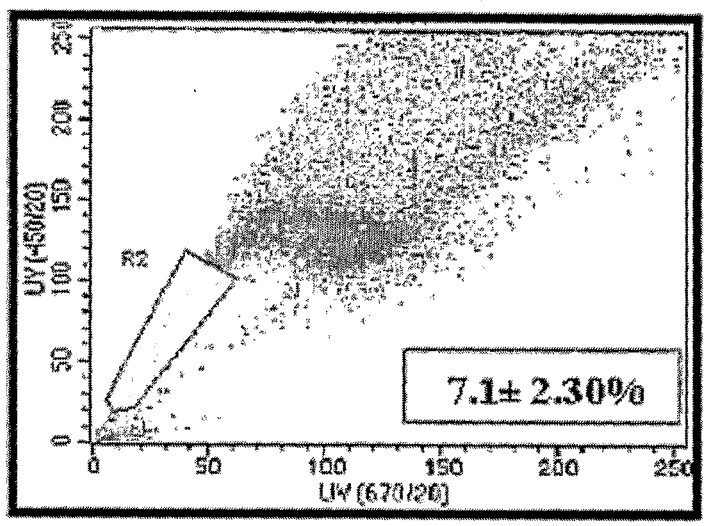
Figure 1B:
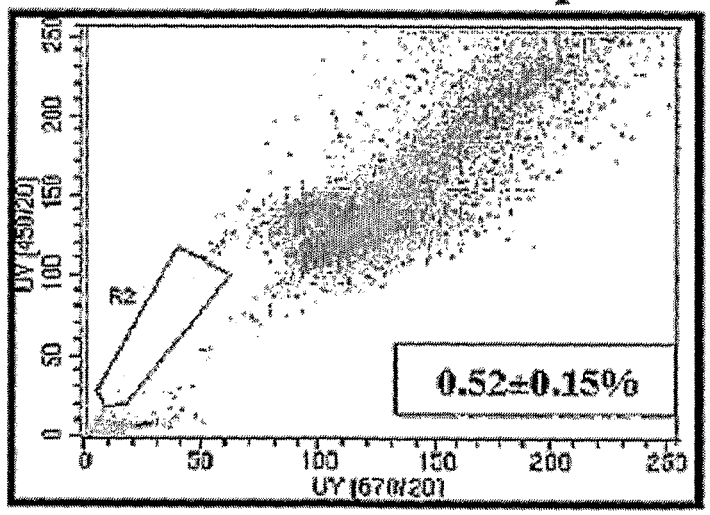

FACS analysis for SP progenitors, which possess the ability to efflux Hoechst 33342 dye, showed these cells in the lower left frame (FIG. 1B-a). After blockage of the efflux pump by verapamil, this gated population disappeared, confirming the presence of approx 6.54% positive SP in the isolated newborn liver cell population (n=4) (FIG. 1B-b). It is known that the SP phenotype is linked to progenitor cells, such as hematopoeitic and oval cells.

Immunostaining revealed that 70±4% of the isolated newborn liver cells were positive for albumin and only 10±2% positive for CK18 (a marker for mature hepatocytes) (data not shown). Taken together, the isolated newborn liver cell population is composed mostly of proliferating hepatoblasts as well as a small population of progenitor cells as hematopoeitic and oval cells.

Example 2

Cell Morphology and Maturation in Adhesive vs. Non-Adhesive Porous Scaffolds

Figure 2A:
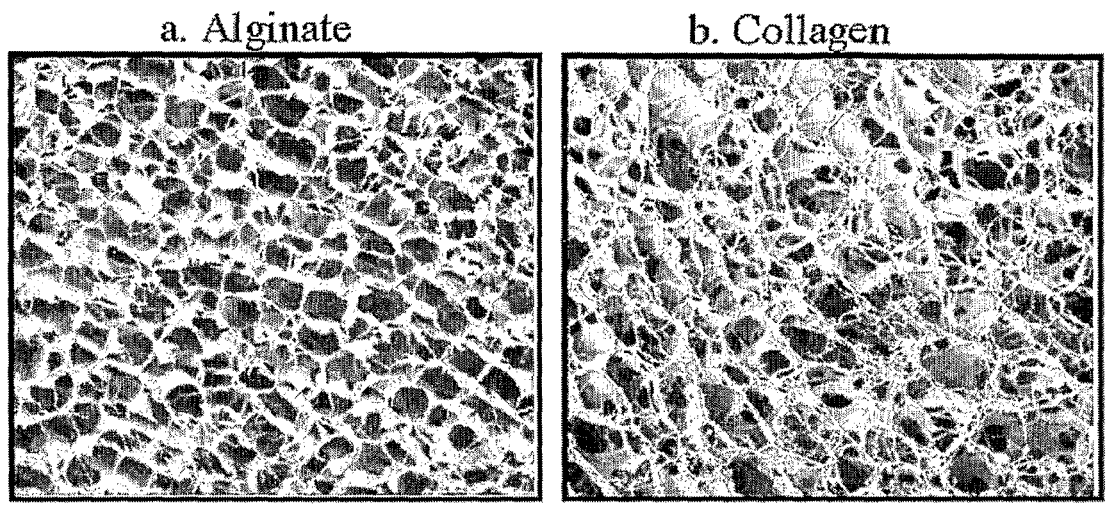
FIG. 2A shows comparable pore size and structure in alginate (a) versus collagen (b) scaffolding.

Post-isolation and characterization, cells were plated within 3-D scaffolds, which possess similar internal macroporous architecture (FIG. 2Aa,b), however differ in their ability to promote cell-matrix interactions. While collagen interacts with cell surface integrins expressed on cell surfaces, alginate is inert, thus promotes fewer cell-matrix and relatively more cell-cell interactions.

Three Days Post-Seeding

Figure 2B:
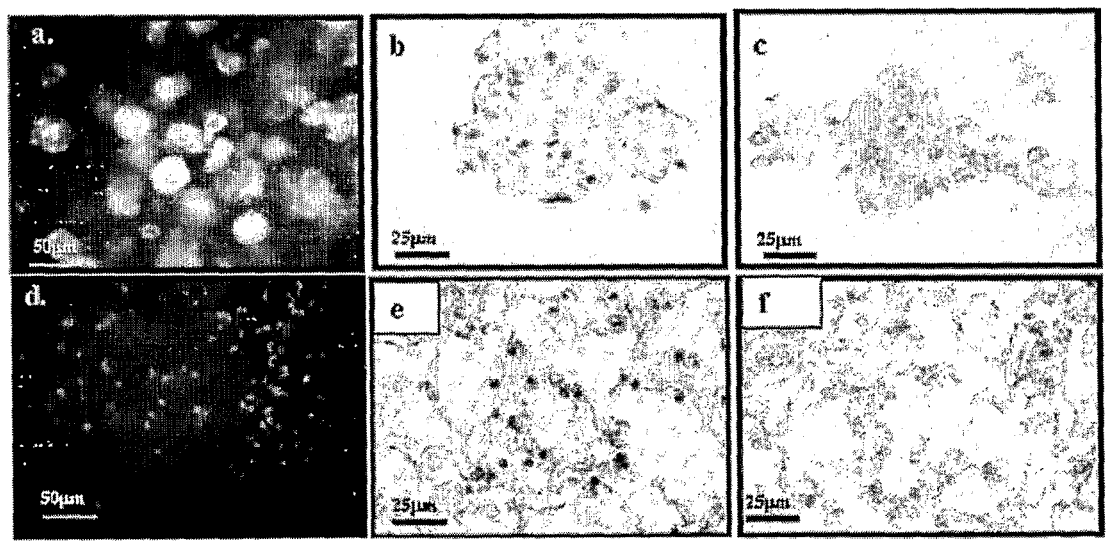
FIG. 2B shows cell morphology and organization within non adherent alginate scaffolds (a-c) compared to adherent collagen (d-f) (seeding density: $125 \times 10^6$ cells/cm$^3$) at 3 days post-seeding. 2B (a, d) shows FDA staining for viable cells; (b, c) shows thin sections stained with H & E within alginate scaffolds; (e.f) shows thin sections stained with H & E within collagen scaffolds.

The newborn liver cell population was seeded in the 3-D macro-porous alginate and collagen scaffolds, with a cell density of $125\times10^6$ cells/cm$^3$. Three days post-seeding, the cell constructs grossly showed different cell morphology as judged by the fluorescence staining of viable cells with FDA and histology (FIGS. 2Ba and 2Bd). In higher magnification images, the alginate-seeded cells stained with H&E (FIG. 2Bb) formed tightly packed spheroids with a mean diameter of 83.7±16.7 µm, whereas within the collagen scaffolds (FIG. 2Be) the cell nucleus appeared adjacent to the collagen matrix. This was also confirmed by staining with Masson trichromica, which stains cell cytoplasm red and collagen blue. In alginate the red cells aggregated are visible and the alginate scaffold wall was not stained (FIG. 2Bc). However, the cells within collagen were lined adjacent to the blue stained collagen matrix filament (FIG. 2Bf).

Figure 2C:
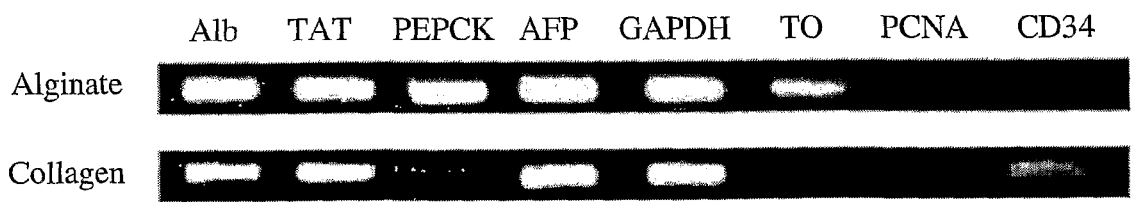
FIG. 2C presents short-term gene expression in adherent and non-adherent cultures at 3 days post seeding. Alginate-based cell constructs expressed adult-specific enzymes (e.g. TO, TAT and PEPCK), whereas the collagen-based cell constructs expressed TAT and albumin.

Gene expression analysis (FIG. 2C) indicated that on day 3 post-seeding within the alginate scaffolds, the cells expressed the adult liver-specific enzymes PEPCK, TAT and TO. In contrast, the cells adhered to the collagen scaffolds expressed only TAT but no PEPCK and TO. Furthermore, CD34+ cells were present within the collagen-based cell constructs. These findings imply that the adherent collagen scaffolds attenuate cell differentiation and maturation towards hepatocytes.

Six-Week Cultivation

Figure 3A:
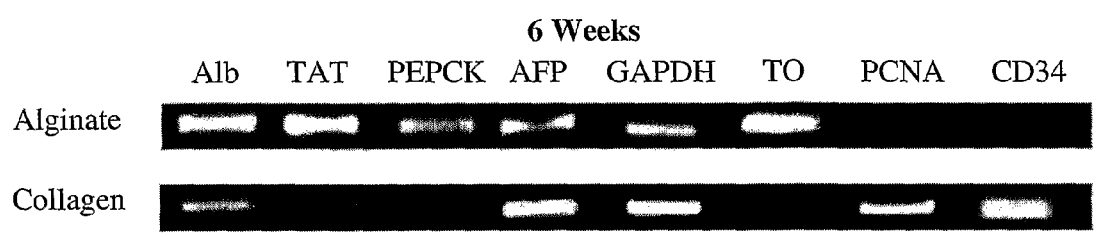
FIG. 3A presents long-term gene expression in adherent vs. non-adherent cultures at 6 weeks post-seeding. Cell constructs were cultivated for 6 weeks. Collagen-based cell cultures had low expression of TAT, while they significantly expressed CD34, PCNA and AFP. In contrast, the alginate-based cell constructs expressed high levels of adult liver specific enzymes, whereas PCNA and CD34 were absent.
Figure 3B:
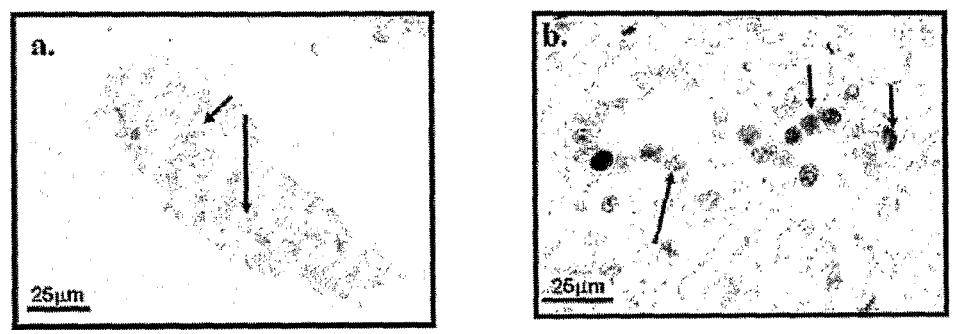
FIG. 3B presents PCNA immunostaining in adherent and non-adherent cultures at 6 weeks post seeding. (a). Spheroid within alginate based scaffold. (b). Adhered cells within collagen based scaffold. Arrows point towards positively stained nuclei.

After 6 week-cultivation, the cellular constructs within alginate scaffolds sustained the expression of adult liver-specific enzymes PEPCK, TAT and TO as well as albumin, while the adherent cells in the collagen scaffolds expressed mainly progenitor and proliferating cell markers as CD34, AFP and PCNA (FIG. 3A). Immunostaining for PCNA (FIG. 3B) confirmed the extensive cell proliferation within collagen-based (FIG. 3Bb) constructs compared to alginate-based (FIG. 3Ba) constructs (68±5.4% vs. 16±2.4%; collagen vs. alginate sections, respectively). The data presented displayed significant statistical differences as determined by the Student's t-test (n=12; $p<0.05$).

Example 3

Organoid Formation in Alginate-based Cellular Constructs

Figure 4:
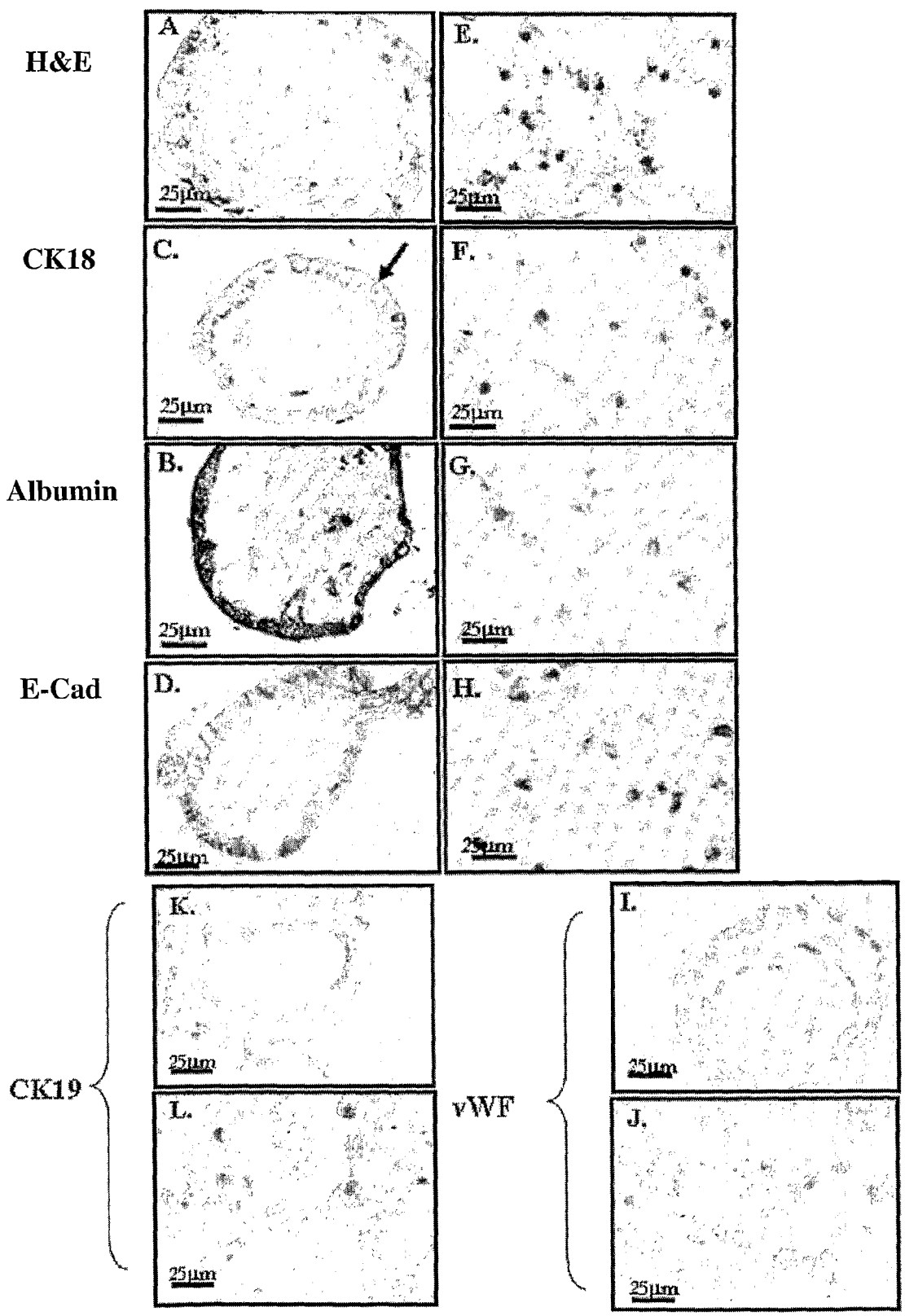
FIG. 4, panels A-L, demonstrate histology and immunocytochemistry of alginate based constructs at 6 weeks post seeding. The spheroids within alginate consisted of hepatocyte monolayer encasing an internal layer of dispersed cells embedded in ECM matrix (panel A; H&E). Immunocytochemistry was carried out to detect differentiated hepatocytes, utilizing antibodies against albumin (panel B) and CK18 (panel C). In addition, epithelial cell-cell interactions were explored by staining for epithelial cadherin (panel D; E-Cadherin). Panels E-H of FIG. 4 show H&E staining, staining for CK18, staining for albumin, and staining for E-cadherin, respectively, in collagen constructs. Panels I and J of FIG. 4 show staining for von Willebrand factor in alginate (panel I) and collagen (panel J) constructs. Panels K and L of FIG. 4 show staining for CK19 in alginate (panel K) and collagen (panel L) constructs.

By 6 weeks in culture, the spheroids in the alginate constructs developed into organoids, wherein the cells were segregated into two main layers; an external cell monolayer enclosing an internal layer of dispersed cells embedded in ECM matrix (FIG. 4, panels A-D). In FIG. 4, panel A, the H&E stained cross section shows that the cells composing the external monolayer have a cuboidal shape, characteristic of mature hepatocytes. By immunohistochemistry, these cells were positively stained for albumin (FIG. 4, panel B) and the mature hepatocyte marker, CK18 (FIG. 4, panel C). A strong positive staining for the cell adhesion molecule, E-cadherin, was apparent in-between the cells constituting the external epithelial cell layer (FIG. 4, panel D). In the collagen constructs, on the other hand, no such structures were formed; the cells remained adhered to the matrix (FIG. 4, panel E) and immunostaining was negative for albumin, E-cadherin and CK18 (FIG. 4, panels F-H). In both alginate (FIG. 4, panels I and K) and collagen (FIG. 4, panels J and L) constructs, immuno-staining for CK19 or von Willebrand factor (vWF), the markers for bile duct cells and endothelial cells (EC), respectively, was negative.

Figure 5:
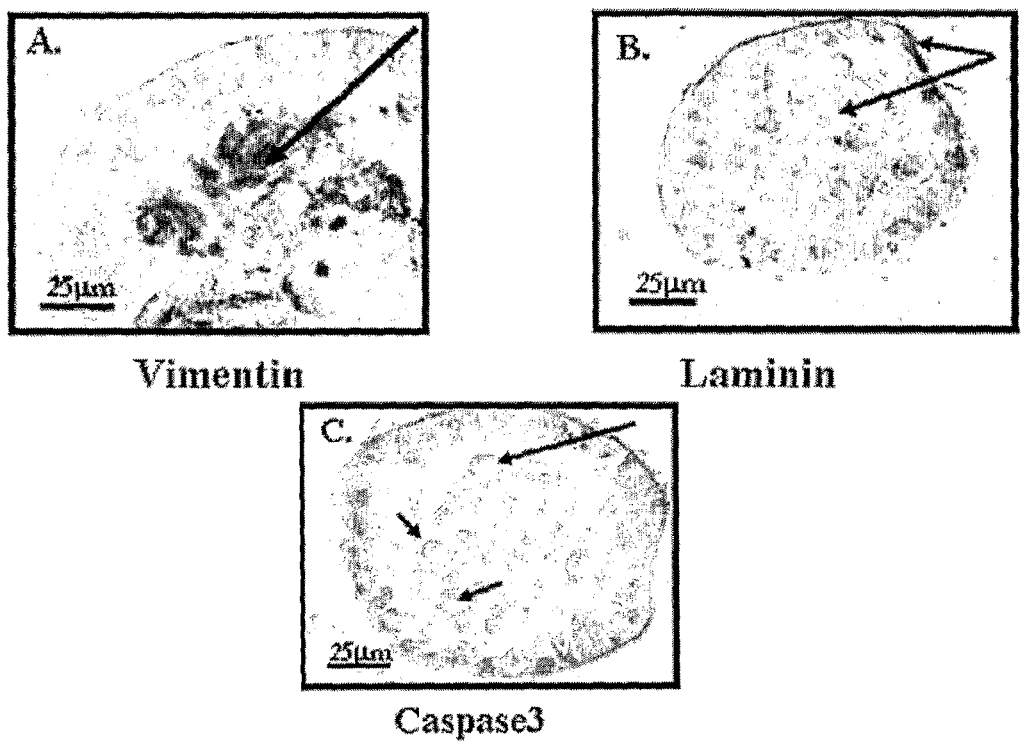
FIG. 5 shows immunostaining for ECM deposition and fibroblasts. Vimentin staining for fibroblasts confirmed their localization in the central cell mass of the alginate-borne spheroid (A) at 6 weeks post seeding. Laminin deposition was concentrated in the spheroid lumen (B). Black arrowheads point towards positive laminin/vimentin staining, while white arrowheads point towards hepatic cell lining. (C) Detection of apoptotic cells within 6 week alginate cultures. Immunostaining for cleaved caspase 3, which indicates the presence of apoptotic cells within the acinar lumen.

In contrast to the external hepatocyte monolayer, the cells in the internal layer were positively stained for vimentin, a fibroblast-like cell marker (FIG. 5A) and they were embedded in a laminin-rich matrix (FIG. 5B), as judged by immunostaining for this ECM component (FIG. 5B). Since hepatocytes rarely secrete large insoluble quantities of deposited laminin, the vimentin-positive cells in this location secreted the laminin. A thin film of laminin covered also the external layer of the hepatocytes, possibly functioning as the basement for the hepatic layer. The internal cell mass contained some apoptotic cells within the acinar lumen according to the light brown staining for cleaved caspase 3 (FIG. 5C).

Figure 6:
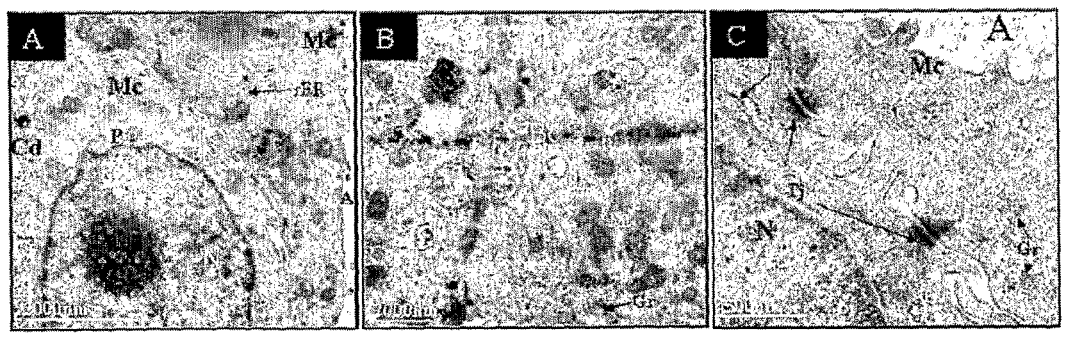
FIG. 6 presents an ultrastructural analysis of alginate—vs. collagen-based cell constructs at 6 weeks post seeding. The hepatocyte cell layer presented cell polarity as judged by the presence of Microvilli (Mc) upon the baso-lateral surface facing the scaffold wall (A-C), as well as an abundance of bile canaliculi (Bc) lined with microvilli and bordered with tight junctions (Tj). The hepatocytes presented metabolic ultra-structures (A-F) as Mitochondria (Mt), Lysosomal vesicles (Ls), Glycogen rosettes (Gr), Rough Endoplasmic Reticulum (rER), Lipid props (L), Peroxisymal vesicles (P) and well defined nucleus (N). (A) shows collagen deposition (Cd) on the opposite side of the cell lining and towards the inner cell mass, as evidenced by condensed black drops at this location. (G, H) Cells within collagen constructs at 6 weeks post-seeding, adjacent to collagen wall (C). All cells seeded within collagen scaffolds possessed an abundance of lipid drops (L) and secondary lysosomal vesicles (SL; H, I), indicative of cell necrosis. Moreover, no polar ultrastructural features were detected in cell-seeded collagen constructs. (G) Two adjacent cells are lined on the collagen scaffold wall, possessing no tight junction at 6 weeks post-seeding.
Figure 6:
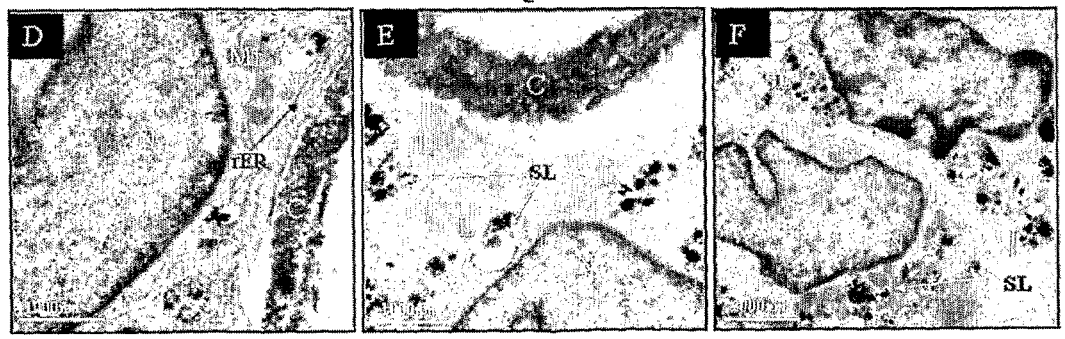

TEM analysis (FIG. 6A-F) revealed that the external hepatocyte layer featured an extensive polarity as seen by the development of apical and baso-lateral surfaces. The apical surface was characterized by microvilli (Mc)-lined bile canaliculi (Bc) and bordered by tight junctions (Tj) between adjacent cells (FIGS. 6A, B & C). The baso-lateral surface separated from the alginate scaffold wall (denoted by A) by deposits of laminin (FIG. 6C), confirmed by laminin immunohistochemistry (FIG. 5B).

This surface possessed an abundance of microvilli (Mc) typical to adult hepatocyte surface. In contrast, no Mc were was apparent on the opposite surface, facing the inner embedded cells. In between the external layer and the inner embedded cell mass, deposits of collagen (Cd) in the form of condensed black drops were seen (FIG. 6A-C). The hepatocytes appeared to be fully functional; having glycogen deposits (Gr), mitochondria (Mt), rough endoplasmic reticulum (rER), lysosomal vesicles (Ls), lipid droplets (L), peroxisomal vesicles (P) and defined nucleus (N).

In the collagen-based constructs (FIGS. 6D, E, F), the cells were adhered to the collagen wall (C; FIGS. 6D and 6E) and no ECM deposits were seen. Polarity, cell-cell contacts, and ultrastructural metabolic features of mature hepatocytes were less distinct compared to the structures in the alginate-based constructs.

Example 4

Hepatocellular Functions

Figure 7:
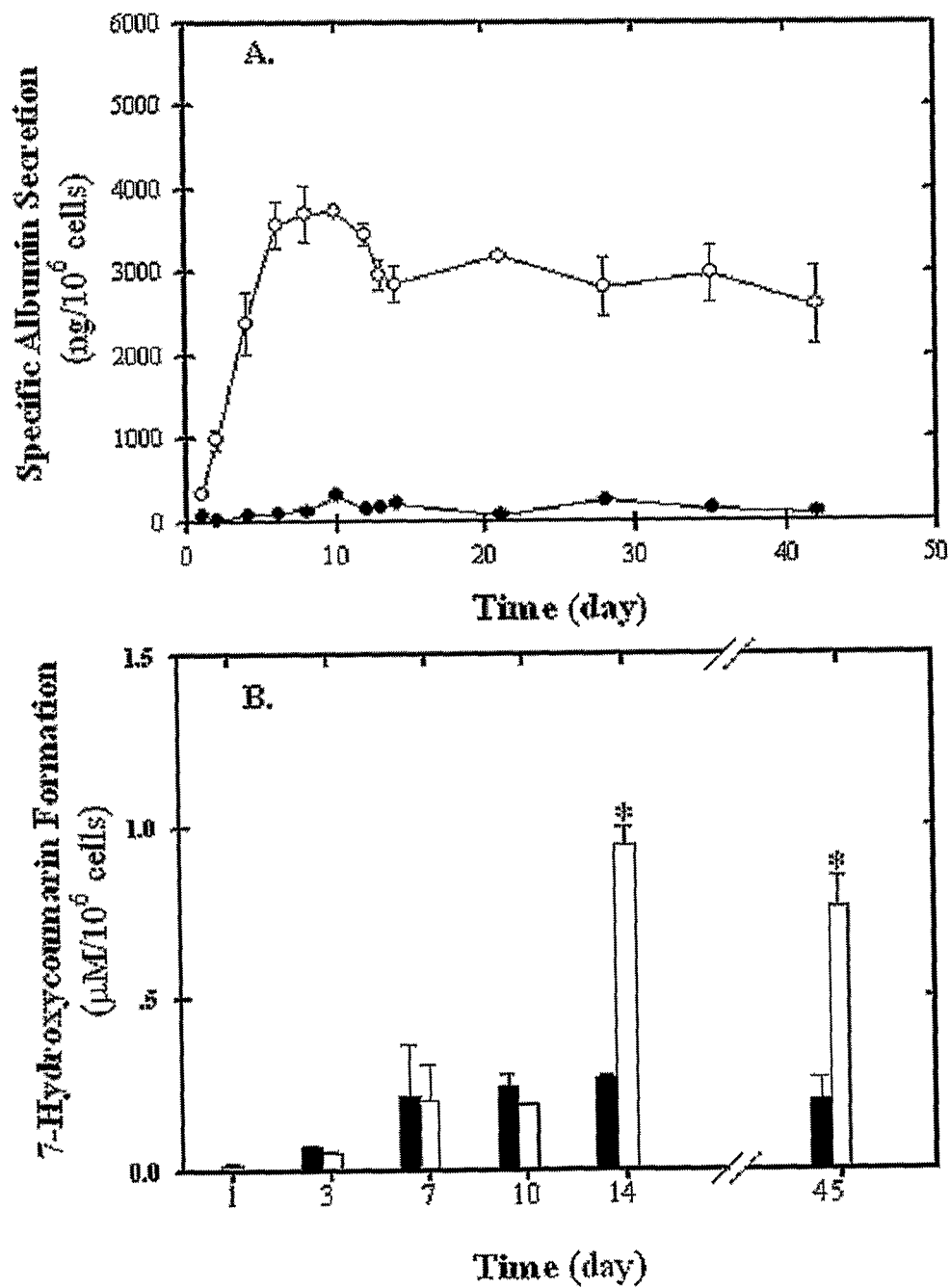
FIG. 7 presents measures of hepatocellular function in the cell construct seeded at a final cell density of $125 \times 10^6$ cells/cm$^3$. With cell differentiation, maturation and organization to hepatic spheroids, the specific albumin secretion rate increased to a maximal level by the 7$^{th}$ day in culture, and was sustained at this level for the duration of culture (FIG. 7, panel A, open circles). In contrast, in the collagen scaffold (filled circles), albumin secretion was negligible throughout the 6 weeks of culture. In addition, 7-Hydroxycoumarin formation, associated with a wide range of phase I isoenzymes (i.e. CYP2B6, CYP2A6, CYP2E1, CYP1A1) [Krasteva N, Seifert B, Albrecht W, Weigel T, Schossig M, Altankov G, Groth T. Influence of polymer membrane porosity on C3A hepatoblastoma cell adhesive interaction and function. Biomaterials. 2004 June; 25(13):2467-76. Behnia K, Bhatia S, Jastromb N, Balis U, Sullivan S, Yarmush M, Toner M. Xenobiotic metabolism by cultured primary porcine hepatocytes. Tissue Eng. 2000 October; 6(5):467-79)], was significantly higher from the second week of culture in alginate-based constructs (FIG. 7, panel B, open bars) compared to that in the collagen-based constructs (filled bars). Both assays expressed statistically significant differences between the above values (Students t-test, n=12, p<0.05).

With cell differentiation, maturation and organization to hepatic spheroids, the specific albumin secretion rate increased to a maximal level by the 7th day in culture, and was sustained at this level for the duration of culture. In contrast, in the collagen scaffold, albumin secretion was negligible throughout the 6 weeks of culture (FIG. 7, panel A). In addition, 7-Hydroxycoumarin formation, representing phase I activity associated with a wide range of phase I isoenzyme activity (i.e. CYP2B6, CYP2A6, CYP2E1, CYP1A1), was significantly higher from the second week of culture in alginate-based constructs compared to that in the collagen-based constructs (FIG. 7, panel B). Both assays demonstrated statistically significant differences between albumin secretion and hydroxycoumarin formation in alginate vs. collagen-based constructs (Students t-test, n=12, p<0.05).

Cellularity as detected by DAPI assay revealed that 84.2±11.8% of the initially seeded cells was retained in alginate scaffolds vs. 95±7.8% in collagen scaffolds, throughout the 6 weeks of culture. These data indicate no significant statistical difference in cellularity between two cultivation treatments (Student's t-test, n=12, p<0.05).

Example 5

Organoid Formation from Progenitor Cell Spinning

Isolation of liver cells is conducted as described in Example 1. Mature hepatocytes are harvested from 4-6-week-old male Sprague-Dawley rats, weighing 180-250 g by the modified three-step in situ collagenase perfusion method (Berry and Friend, 1969, J Cell Biol 43: 506-520.), and purified by isodensity Percoll centrifugation. The cells are inoculated into separate 250 mL spinners at a cell concentration of $5 \times 10^5$ cells/mL and a final volume of 100 mL culture medium. Prior to cell seeding, the vessels are siliconized by coating with Sigmacote (Sigma) for 1 hour, then rinsed with deionized water and sterilized. The cell-seeded vessels are stirred at 110 rpm in a 37° C., humidified, 5% $CO_2$ incubator. For analysis, the spheroids and organoids are collected from the medium by gravitation.

The cells are also separately inoculated into 25 mL T-flasks at cell concentration of $5 \times 10^5$ cells/mL and a final volume of 4 mL medium. The T-flasks are placed on an orbital incubator (70 rpm) at 37° C., with humidified air containing 5% $CO_2$. For analysis, the spheroids are similarly collected.

Gene expression analysis for adult liver-specific enzymes TAT, PEPCK, and TO is conducted as described above, as are histologic assessment, and assays for hepatocellular function. Comparative data is obtained for spheroid formation and activity in cultures of immature hepatic progenitor cells versus differentiated hepatocytes. Organoid formation in the former cultures is evaluated as well as any absence of formation in hepatocyte cultures.

---

What is claimed is:

1. An epithelial organoid comprising;
   a. an aggregate of epithelial cells derived from the liver, wherein said cells predominantly express markers associated with differentiated hepatocyte cell types; or
   b. an aggregate of epithelial cells, wherein said aggregate assumes a structure or performs a function associated with the liver or a fragment thereof; or
   c. a combination thereof;
   wherein said organoid is formed in vitro,
   wherein said organoid comprises cells exhibiting hepatocyte-specific morphology, or at least one hepatocellular function, or a combination thereof,
   wherein more than 95% of said cells are viable in said organoid,
   wherein said organoid comprises at least 84.2% of cells originally seeded in vitro; and
   wherein said organoid is formed by in vitro culture of progenitor cells derived from a liver on a macroporous polyanionic polysaccharide-based scaffold.

2. The organoid of claim 1, wherein said organoid is formed by in vitro culture of said cells derived from a liver on a macroporous alginate scaffold having a pore size of 50 to 100 microns.

3. The organoid of claim 1, wherein said organoid comprises cells expressing tyrosine amino transferase (TAT), a phosphoenolpyruvate kinase (PEPCK), a tryptophan oxygenase (TO), or a combination thereof.

4. The organoid of claim 1, wherein said organoid is formed by applying a progenitor cell population enriched for hepatic, precursor cells to a macroporous poly anionic polysaccharide-based scaffold and culturing said scaffold in vitro for a period of time sufficient to form said organoid.

* * * * *

SEQUENCE LISTING

```
<160> NUMBER OF SEQ ID NOS: 16

<210> SEQ ID NO 1
<211> LENGTH: 20
<212> TYPE: DNA
<213> ORGANISM: Homo sapiens

<400> SEQUENCE: 1
ttcctgaagc tcagagactg                                                   20

<210> SEQ ID NO 2
<211> LENGTH: 20
<212> TYPE: DNA
<213> ORGANISM: Homo sapiens

<400> SEQUENCE: 2
tggcgaagca gttatccttg                                                   20

<210> SEQ ID NO 3
<211> LENGTH: 22
<212> TYPE: DNA
<213> ORGANISM: Homo sapiens

<400> SEQUENCE: 3
atttcccgga attcgagaac ga                                                22

<210> SEQ ID NO 4
<211> LENGTH: 22
<212> TYPE: DNA
<213> ORGANISM: Homo sapiens

<400> SEQUENCE: 4
gacgggtgag ggcttatttg tc                                                22

<210> SEQ ID NO 5
```

-continued

<210> SEQ ID NO 5
<211> LENGTH: 20
<212> TYPE: DNA
<213> ORGANISM: Homo sapiens

<400> SEQUENCE: 5
ccagccagag tatattcaca                                                20

<210> SEQ ID NO 6
<211> LENGTH: 20
<212> TYPE: DNA
<213> ORGANISM: Homo sapiens

<400> SEQUENCE: 6
gctttctcga agtcctcttc                                                20

<210> SEQ ID NO 7
<211> LENGTH: 21
<212> TYPE: DNA
<213> ORGANISM: Homo sapiens

<400> SEQUENCE: 7
tgcccgacag agaaaaatat g                                              21

<210> SEQ ID NO 8
<211> LENGTH: 21
<212> TYPE: DNA
<213> ORGANISM: Homo sapiens

<400> SEQUENCE: 8
gcagtttctg gaaagtggaa g                                              21

<210> SEQ ID NO 9
<211> LENGTH: 19
<212> TYPE: DNA
<213> ORGANISM: Homo sapiens

<400> SEQUENCE: 9
tggtgctgag tatgtcgtg                                                 19

<210> SEQ ID NO 10
<211> LENGTH: 19
<212> TYPE: DNA
<213> ORGANISM: Homo sapiens

<400> SEQUENCE: 10
tggcatggac tgtggtcat                                                 19

<210> SEQ ID NO 11
<211> LENGTH: 20
<212> TYPE: DNA
<213> ORGANISM: Homo sapiens

<400> SEQUENCE: 11
tgtagttcag agacgtgatg                                                20

<210> SEQ ID NO 12
<211> LENGTH: 20
<212> TYPE: DNA
<213> ORGANISM: Homo sapiens

<400> SEQUENCE: 12
gaactgctca ccaagcttta                                                20

```
<210> SEQ ID NO 13
<211> LENGTH: 20
<212> TYPE: DNA
<213> ORGANISM: Homo sapiens

<400> SEQUENCE: 13
tcccagacaa gcaatgttga                                                    20

<210> SEQ ID NO 14
<211> LENGTH: 20
<212> TYPE: DNA
<213> ORGANISM: Homo sapiens

<400> SEQUENCE: 14
aggtacaaac ttggtgacag                                                    20

<210> SEQ ID NO 15
<211> LENGTH: 20
<212> TYPE: DNA
<213> ORGANISM: Homo sapiens

<400> SEQUENCE: 15
actttccagc aaactccagc                                                    20

<210> SEQ ID NO 16
<211> LENGTH: 20
<212> TYPE: DNA
<213> ORGANISM: Homo sapiens

<400> SEQUENCE: 16
agcaggactc ccgaggtaac                                                    20
```